US008669118B2

(12) United States Patent
Kaufman et al.

(10) Patent No.: US 8,669,118 B2
(45) Date of Patent: Mar. 11, 2014

(54) METHODS AND SYSTEMS FOR COLLECTING CELLS OF A BIOLOGICAL SPECIMEN

(75) Inventors: Howard B. Kaufman, Newton, MA (US); Barry Hunt, Andover, MA (US)

(73) Assignee: Hologic, Inc., Bedford, MA (US)

( * ) Notice: Subject to any disclaimer, the term of this patent is extended or adjusted under 35 U.S.C. 154(b) by 725 days.

(21) Appl. No.: 12/558,400

(22) Filed: Sep. 11, 2009

(65) Prior Publication Data

US 2011/0062087 A1 Mar. 17, 2011

(51) Int. Cl.
*G01N 1/10* (2006.01)
(52) U.S. Cl.
USPC .............................. 436/177; 436/174; 436/63
(58) Field of Classification Search
USPC ........ 436/63, 174, 177; 73/53.01, 64.56, 863, 73/863.01, 863.02, 863.03, 863.21, 73/863.23, 864.34, 863.24; 435/30, 40, 435/51, 173.9, 261, 286.1, 286.5, 308.1, 29, 435/283.1; 210/739, 744, 745, 96.1, 96.2, 210/97, 103, 137, 741; 422/500, 501, 509, 422/513, 527, 534, 535, 536, 112
See application file for complete search history.

(56) References Cited

U.S. PATENT DOCUMENTS

| 5,143,627 | A | 9/1992 | Lapidus et al. |
| 5,364,597 | A | 11/1994 | Polk, Jr. et al. |
| 5,772,818 | A | 6/1998 | Polk, Jr. et al. |
| 6,318,190 | B1 | 11/2001 | Radcliffe et al. |
| 6,572,824 | B1 | 6/2003 | Ostgaard et al. |
| 2004/0219073 | A1 | 11/2004 | Radcliffe et al. |
| 2007/0099291 | A1 | 5/2007 | Tenney et al. |
| 2008/0145887 | A1 | 6/2008 | MacIndoe et al. |

FOREIGN PATENT DOCUMENTS

EP   0448837 A2   10/1991

OTHER PUBLICATIONS

PCT International Search Report and Written Opinion for PCT/US2010/048117, Applicant CYTYC Corporation, Forms PCT/ISA/210, 220, and 237, dated Feb. 7, 2011 (10 Pages).

*Primary Examiner* — Christopher A Hixson
(74) *Attorney, Agent, or Firm* — Vista IP Law Group LLP

(57) ABSTRACT

Methods and systems for collecting cells on a filter disposed in a specimen fluid containing suspended cells of a biological specimen. A short vacuum pulse is applied across a filter to sip specimen fluid. A percentage or portion of the filter surface area covered by cells is determined is representative of or correlates to the density of cells in the specimen fluid. A maximum vacuum amplitude and/or duration are determined utilizing the determined filter coverage. A longer, continuous vacuum or slurp is applied across the filter to collect cells on the filter while limiting the amplitude and/or duration of the slurp based at least in part upon the determined maximum vacuum amplitude and/or duration.

20 Claims, 25 Drawing Sheets

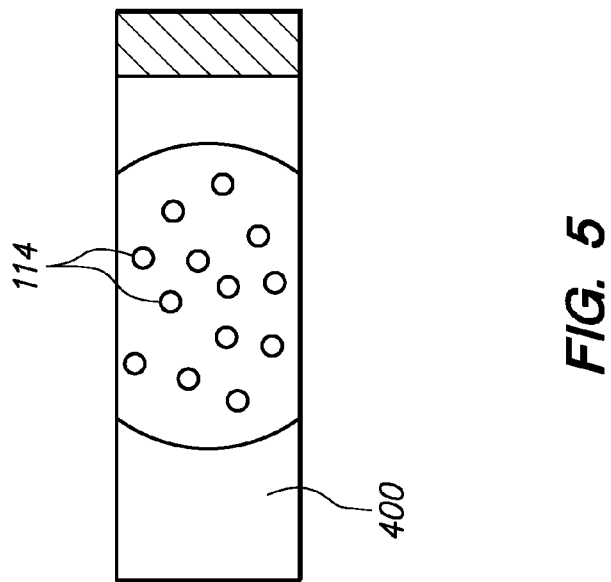
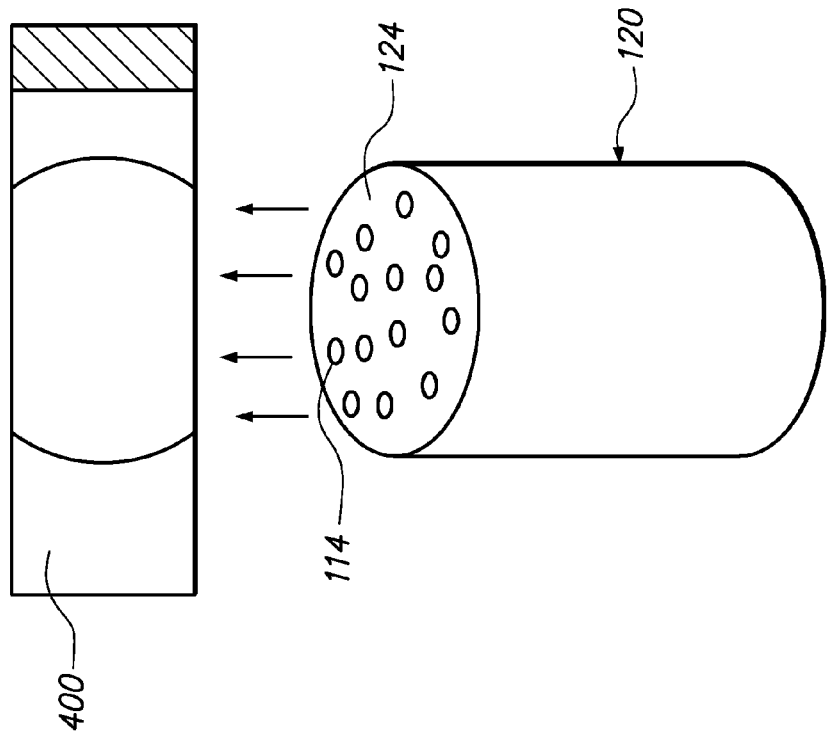

During Slide Preparation

During Slide Preparation

| Percentage of Cells on slide in Cluster >= 40 | | | | | | |
|---|---|---|---|---|---|---|
| w/Continuous Vac / Slurp | | | | Std T5 | | |
| Slurp duration | Slide #: | | | Slide #: | | |
| 5-sec | D_4 | 8.0% | | D_2 | 7.1% | |
| 30-sec | H_12, H_13, H_14 | 6.5% | | H_1, H_2, H_3 | 5.2% | |
| 48-sec | J_18, J_19, J_20 | 8.2% | | J_1, J_2, J_3 | 5.7% | |
| 55-sec | E_7, E_10 | 4.5% | | E_3 | 4.7% | Δ |
| | Average: | 6.8% | | Average: | 5.7% | 1.1% |
| | Std Deviation: | 1.7% | | Std Deviation: | 1.0% | |

FIG. 14A

| Total Cell Count on slide | | | | | | |
|---|---|---|---|---|---|---|
| w/Continuous Vac / Slurp | | | | Std T5 | | |
| Slurp duration | Slide #: | | | Slide #: | | |
| 5-sec | D_4 | 112,908 | | D_2 | 99,706 | |
| 30-sec | H_12, H_13, H_14 | 91,177 | | H_1, H_2, H_3 | 88,458 | |
| 48-sec | J_18, J_19, J_20 | 97,029 | | J_1, J_2, J_3 | 92,003 | |
| 55-sec | E_7, E_10 | 61,946 | | E_3 | 48,702 | Δ |
| | Average: | 90,765 | | Average: | 82,217 | 8,547 |
| | Std Deviation: | 21,294 | | Std Deviation: | 22,832 | |

FIG. 14B

| Last Updated BL29 Process Times | | | | | | Slurp Time savings | |
|---|---|---|---|---|---|---|---|
| T2 Sips | T5 Sips | BL29 Proc Time | Deaconess Distribution | Real World Total Proc Time | | Estimated Aspiration time savings (sec) | Estimated BL29 Proc Time w/slurping (sec) |
| 5 | 6 | 111 | 17.3 | 1,920 | secs | | 111 |
| 10 | 10 | 112 | 21.1 | 2,363 | secs | | 112 |
| 15 | 16 | 120 | 17.3 | 2,076 | secs | | 114 |
| 20 | 21 | 126 | 8.51 | 1,072 | secs | 6.0 | 119 |
| 25 | 27 | 136 | 5.9 | 802 | secs | 7.2 | 128 |
| 30 | 33 | 140 | 2.83 | 396 | secs | 8.4 | 130 |
| 35 | 40 | 131 | 2.34 | 307 | secs | 9.6 | 121 |
| 40 | 47 | 140 | 2.21 | 309 | secs | 10.5 | 128 |
| 45 | 54 | 136 | 1.72 | 234 | secs | 11.7 | 125 |
| 50 | 62 | 143 | 1.6 | 229 | secs | 11.0 | 131 |
| 60 | 78 | 151 | 2.09 | 316 | secs | 12.2 | 138 |
| 75 | 100 | 157 | 2.59 | 407 | secs | 13.4 | 142 |
| 100 | 130 | 156 | 1.35 | 211 | secs | 14.6 | 140 |
| 130 | 155 | 179 | 3.07 | 550 | secs | 15.8 | 162 |
| 170 | 179 | 179 | 1.36 | 243 | secs | 17.3 | 161 |
| 250 | 200 | 183 | 8.73 | 1,598 | secs | 18.5 | 161 |
| | | | | 13,032 | secs | 22.0 | |
| | | | 100 | 130.3 | secs/vial | | |

Per Carousel Overhead Time: 52 secs
Total Carousel Time: 2658 secs
Vials/Hour: 27.1  Vials/Hour: 28.6

Table 4

METHODS AND SYSTEMS FOR COLLECTING CELLS OF A BIOLOGICAL SPECIMEN

BACKGROUND

Medical professionals and technicians often review biological specimen slides in order to analyze whether a patient has or may have a particular medical condition or disease. For example, a cytological specimen on a slide may be prepared and examined to determine the presence of malignant or pre-malignant cells as part of a Papanicolaou (Pap) smear test, or other cancer detection tests. For this purpose, collected cells can be stored in a liquid preservative, and a slide having cells of the specimen can be prepared using a filter transfer technique, as described in U.S. Pat. Nos. 6,572,824, 6,318,190, 5,772,818, 5,364,597 and 5,143,627 and U.S. Publication Nos. 2008/0145887 and 2007/0099291, the contents of which are expressly incorporated herein by reference as though set forth in full.

For example, one known automated slide preparation system includes a container or vial that holds a cytological specimen having tissue or cells in solution. An end of a filter or membrane is inserted into the fluid, and short pulses of vacuum are applied to draw short "sips" of fluid into the filter cartridge. The vacuum pressure decays as cell containing fluid is drawn across the membrane and into the filter cartridge to collect cells on the filter. The "decay" of this temporary pressure drop, specifically the change in pressure inside of the filter over time, is used to calculate the amount of cells collected on the filter or membrane or the "membrane occlusion percentage". The vacuum level decays faster when the membrane has no cells or only a few cells compared to when the membrane has collected a larger number of cells. Other systems utilize a mass air flow sensor to detect filter coverage rather than vacuum decay. This is done by detecting the rate of air flow through the filter and through the air flow sensor. The air flow rate changes as cells are collected on the filter. The air flow rate is higher when no cells or only a few cells are on the filter and decreases as the filter becomes increasingly clogged with cells.

While current systems and methods for applying cells to a specimen slide using filter transfer techniques have been effectively utilized to prepare specimen samples on a slide, they have a number of shortcomings in that they do not account for different cellular densities of specimens. Further, attempts to increase processing throughput with certain known systems may lead to application of excessive vacuum to certain specimens and increased cell clustering.

SUMMARY

One embodiment is directed to a method for collecting cells on a filter and comprises positioning the filter in a specimen fluid containing suspended cells of a biological specimen and determining a maximum rate of aspiration of the specimen fluid across the filter by applying initial vacuum across the filter to draw specimen fluid across the filter and determining a percentage of the filter covered by cells as a result of the initial vacuum, the maximum rate of aspiration being based at least in part upon the percentage of the filter covered by cells. The method further comprises applying a continuous vacuum across the filter to collect cells on the filter while controlling amplitude and duration of the continuous vacuum based at least in part upon the determined maximum aspiration rate.

Another embodiment is directed to a method for collecting cells on a filter and comprises positioning the filter in a specimen fluid containing suspended cells of a biological specimen, applying an initial pulse of vacuum to cause pulsatile aspiration of the specimen fluid across the filter, determining a maximum rate of aspiration of the specimen fluid across the filter based at least in part upon a determined percentage of the filter covered by cells as a result of the applied pulsatile aspiration of the specimen fluid across the filter and determining an amplitude and a duration of a continuous vacuum to be applied across the filter based at least in part upon the determined maximum rate of aspiration. The method further comprises applying the continuous vacuum across the filter to collect cells on the filter while controlling the amplitude and duration of the continuous vacuum based at least in part upon the determined amplitude and determined duration.

Another embodiment is directed to a system for collecting cells on a filter disposed in a specimen fluid containing suspended cells of a biological specimen. The system comprises a tubular filter carrier defining an interior chamber, a filter, a vacuum source, a sensor and a controller. The filter is disposed on a distal end of the filter carrier, and the vacuum source is operable to provide vacuum to the interior chamber. In this manner, when the filter carrier and the filter are at least partially disposed in a specimen fluid containing suspended cells of a biological specimen, the cells of the biological specimen are collected against a distal facing surface of the filter. The sensor is associated with the filter, and the controller is configured or operable to determine a maximum rate of aspiration of the specimen fluid across the filter by applying initial vacuum across the filter to draw specimen fluid across the filter and determine a percentage of the filter covered by cells as a result of the initial vacuum, the maximum rate of aspiration being based at least in part upon the percentage of the filter covered by cells. The controller is further configured or operable to apply a continuous vacuum across the filter to collect cells on the filter while controlling amplitude and duration of the continuous vacuum based at least in part upon the determined maximum rate of aspiration.

Another embodiment is directed to a system for collecting cells on a filter disposed in a specimen fluid containing suspended cells of a biological specimen. The system comprises a tubular filter carrier defining an interior chamber, a filter, a vacuum source, a sensor and a controller. The filter is disposed on a distal end of the filter carrier, and the vacuum source is operable to provide vacuum to the interior chamber. In this manner, when the filter carrier and the filter are at least partially disposed in a specimen fluid containing suspended cells of a biological specimen, the cells of the biological specimen are collected against a distal facing surface of the filter. The sensor is associated with the filter, and the controller is configured or operable to apply an initial pulse of vacuum to cause pulsatile aspiration of the specimen fluid across the filter, determine a maximum rate of aspiration of the specimen fluid across the filter based at least in part upon a determined percentage of the filter covered by cells as a result of the applied pulsatile aspiration of the specimen fluid across the filter and determine an amplitude and a duration of a continuous vacuum to be applied across the filter based at least in part upon the determined maximum rate of aspiration. The controller is further operable or configured to apply the continuous vacuum across the filter to collect cells on the filter while controlling the amplitude and the duration of the continuous vacuum based at least in part upon the determined amplitude and the determined duration.

In one or more embodiments, methods and systems are operable or configured to determine maximum aspiration rates to collect cells of different specimens on respective filters using different maximum aspiration rates for the different specimens. Vacuum that is amplitude and/or duration controlled can be applied to aspirate specimen fluid and collect cells on respective filters. With embodiments, the amplitude and/or duration can be adjusted or customized for different specimens, e.g., depending on whether the specimens have different cellular densities. In this manner, stronger and/or longer vacuum can be applied to less dense samples, whereas a weaker and/or shorter vacuum can be applied to denser samples.

In one or more embodiments, maximum aspiration rates and amplitude and/or duration controls of vacuum used to collect the substantial majority of cells on a filter are determined utilizing or based at least in part upon a rate of decay of initial vacuum as cells are collected on the filter or a change of air flow through the filter as cells are collected on the filter.

Further, in one or more embodiments, maximum aspiration rates are determined based on cellular densities rather than the portion or percentage of a surface area of a filter covered by cells. For example, a laser or ultrasound source can be arranged to direct energy into the specimen fluid, and the reflections are indicative of cellular densities, which are used to determine maximum aspiration rates. Other embodiments may involve use determinations of portions or percentages of a filter covered by cells and cellular density measurements using, for example, a laser or other suitable device.

In one or more embodiments, a maximum aspiration rates is determined utilizing initial vacuum or vacuum pulses to perform pulsatile aspiration or "sips" of the specimen fluid across the filter. For example, a portion or percentage of a surface area of the filter covered by cells may be determined during pulstatile aspiration, and the amplitude and/or duration of the vacuum to be applied to collect cells is based at least in part upon the percentage of the filter covered by cells during pulsatile aspiration. Embodiments may involve application of a single aspiration pulse or multiple aspiration pulses, e.g., to intermittently or periodically perform pulsatile aspiration of specimen fluid across the filter. One determination or measurement of filter coverage, e.g., the final determination or measurement, may be selected, and the amplitude and/or duration of vacuum is determined based at least in part upon the selected percentage of the filter surface area covered by cells.

In one or more embodiments, a duration of vacuum or continuous vacuum is substantially longer than a duration of the pulse of vacuum and a duration of the pulsatile aspiration of specimen fluid.

Further, with embodiments, the bulk of cell collection performed during vacuum or continuous vacuum is done without conducting measurements relating to filter coverage. Thus, filter coverage determinations are performed during initial application of vacuum or initial vacuum sips, but not during application of amplitude and/or duration controlled vacuum that is used to continuously collect cells after initial vacuum.

In one or more embodiments, the duration of duration and/or amplitude controlled vacuum is substantially longer than a duration of the initial vacuum, e.g., multiples or multiple times the duration of the initial vacuum or initial pulsatile aspiration. For example, the duration of the initial of vacuum or vacuum pulses is shorter than about two seconds, whereas the duration of the continuous vacuum or amplitude and/or duration controlled vacuum is longer than five seconds. With embodiments, the amount of specimen fluid flowing through the filter during application of the continuous or amplitude and/or duration controlled vacuum is substantially greater than the amount of specimen fluid flowing through the filter during application of the initial vacuum.

In one or more embodiments, an area defined by a curve representing the amplitude of the continuous or amplitude and/or duration controlled vacuum over time is substantially greater than an area defined by a curve representing the amplitude of the initial vacuum or vacuum pulse for pulsatile aspiration over time.

In one or more embodiments, one or more pulses of vacuum may be applied after continuous or amplitude and/or duration controlled vacuum to perform pulsatile aspiration to collect additional cells on the filter until a desired coverage percentage of cells on the filter is obtained. For this purpose, the duration of the continuous or amplitude and/or duration controlled vacuum may be longer than a duration of the short vacuum pulses applied after the continuous vacuum. In this manner, a small number of additional cells (compared to the number of cells collected during continuous or amplitude and/or duration controlled vacuum) can be collected in order to add a small number of cells to the filter.

In one or more embodiments, continuous or amplitude and/or duration controlled vacuum for collecting a substantial majority of cells is formed by or comprised of low duty cycle (e.g., 3-15%) vacuum pulses. These low duty cycle pulses have a duration on the order of milliseconds, which is substantially shorter than a duration of the initial vacuum and substantially shorter than the duration of continuous vacuum (e.g., on the order of seconds).

Thus, with embodiments, the amplitude and/or duration of a continuous vacuum can be dynamically adjusted, controlled and customized for different specimens that may have different cellular densities while providing for enhanced throughput and maintaining or reducing cell clustering. While certain embodiments may involve controlling only amplitude or only duration, embodiments also provide for limiting aspiration rates by controlling both amplitude and duration in order to achieve a balance between vacuum levels and specimen quality or clustering and processing speeds or throughput. These dynamic or customized settings allow cell collection to be performed more quickly while reducing or maintaining the same level of cell clustering and while processing fluid specimens of different cellular densities.

BRIEF DESCRIPTION OF THE DRAWINGS

The foregoing and other aspects of embodiments are described in further detail with reference to the accompanying drawings, wherein:

FIG. 4 illustrates application of cells that have been collected using a cytological filter to a specimen slide;

FIG. 5 illustrates a specimen slide having cells applied by a cytological filter;

FIGS. 14A-C illustrate how embodiments may be used to process specimen slides more quickly with comparable cell clustering compared to a know slide processing system.

DETAILED DESCRIPTION OF ILLUSTRATED EMBODIMENTS

Figure 1:
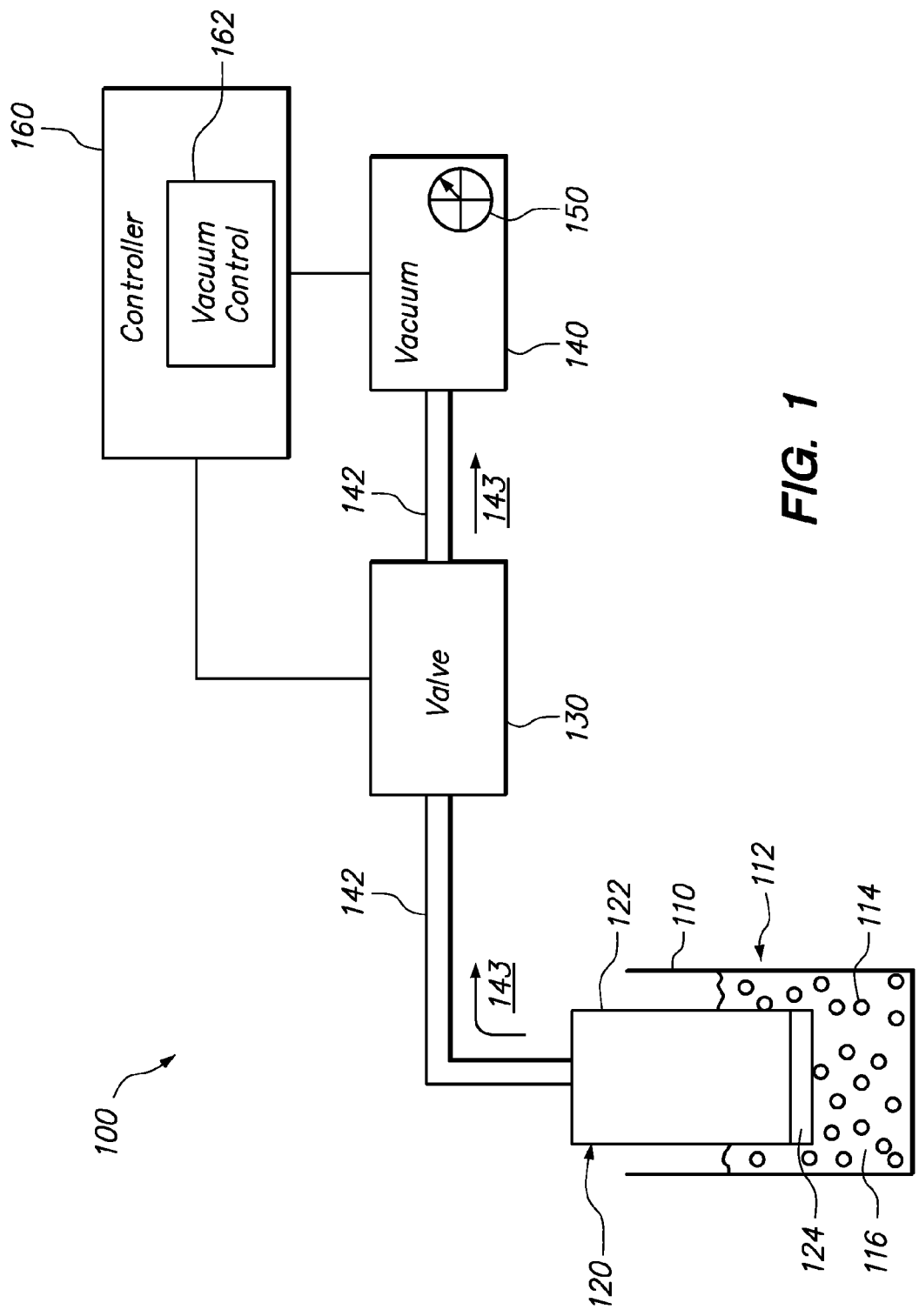
FIG. 1 is a block diagram of a system constructed according to one embodiment that is configured or operable to prepare a specimen slide while limiting the aspiration rate of specimen fluid and that determines filter coverage based on vacuum decay.

Embodiments are related to governing flow or aspiration rates of specimen fluid through a filter. In certain embodiments, one or more vacuum parameters such vacuum amplitude, duration and/or duty cycle of millisecond pulses forming a continuous application of vacuum are controlled. With embodiments, a maximum rate of aspiration of specimen fluid across a filter, which is related to cells collected on the filter, is determined (e.g., empirically), and vacuum parameters such as amplitude and duration are determined based on the maximum aspiration rate. Vacuum is applied across a filter to collect cells while controlling the amplitude and duration based at least in part upon the amplitude and duration.

In certain embodiments, maximum aspiration rates are determined utilizing one or more short vacuum pulses and corresponding short, pulsatile aspirations or "sips" of specimen fluid, during which measurements relating to filter coverage percentages are made. After these initial pulsatile aspirations, a longer, continuous vacuum or "slurp", during which no filter coverage percentage determinations are made, is applied to aspirate specimen fluid and collect a substantial majority of the cells to be collected on the filter. With controls provided by embodiments, desired filter coverage levels are achieved more quickly than known systems while maintaining or reducing the degree of cell clustering and accounting for specimens that have different cellular densities.

Thus, in contrast to known systems and methods that utilize a series of short pulsatile aspirations or "sips" generated by short vacuum pulses, embodiments utilize one or more initial short pulsatile aspirations followed by a longer, continuous aspiration during which vacuum amplitude and duration may be controlled to "slurp" specimen fluid. One or more additional pulsatile aspirations may follow the continuous aspiration resulting from the amplitude and duration controlled vacuum if small numbers of cells are to be added to the filter in order to finely tune the filter coverage.

Further, in contrast to known systems that measure filter coverage during each sip, embodiments employ a different method that involves measuring filter coverage during initial application of vacuum and pulsatile aspiration, e.g., by measuring vacuum decay or changes in air flow, but these pulsatile aspirations are followed by vacuum that may amplitude and duration controlled for substantially longer, continuous aspiration of specimen fluid during which no measurement or determination related to filter coverage is performed. Thus, in certain embodiments, measurements and determinations related to filter coverage percentages are performed only during short pulsatile aspirations that occur before, and possibly after, the longer, continuous aspiration during which a substantial majority of cells are collected such that the continuous aspiration can be dedicated to cell collection. Further aspects of embodiments are described with reference to FIGS. 1-14C.

Referring to FIG. 1, an automated slide preparation system 100 constructed according to one embodiment is configured for processing a container or vial 110 (generally "vial 110") that holds a cytological specimen 112 including tissue and/or cells 114 (generally "cells 114"). The cells 114 are dispersed within a specimen fluid, liquid, solution, suspension, preservative or transport medium 116 (generally "specimen fluid 116"). The cells 114 may be various types of cells including, but not limited to, cells 114 collected during a Pap smear test and other cancer detection tests, and one example of a specimen fluid 116 that may be used is PreserveCyt™, available from Hologic Corporation.

The system 100 includes or utilizes a filter 120 having a tubular filter carrier, body or cartridge 122 defining an interior chamber and a filter material or membrane 124 disposed on a distal end thereof, a valve 130 such as a Quick Turn Open (QTO) valve or other suitable valve, a vacuum source or chamber 140 such as a fixed volume vacuum chamber and associated vacuum tubes or conduits 142, and a sensor or measurement device 150 (generally "sensor 150"). The sensor 150 is associated with, operably coupled to or in communication with the filter 120, and a controller or processing component 160 (generally controller 160) is associated with, operably coupled to or in communication with the valve 130, the vacuum chamber 140 and the sensor 150.

In the embodiment illustrated in FIG. 1, the sensor 150 is a vacuum sensor that can detect how a vacuum level within the filter 120 decays over time. The vacuum decay is representative of the filter 120 coverage or the portion or percentage of the distal face or surface area of the filter element or membrane 124 that is covered by or clogged with cells 114 since the vacuum decay is greater as more cells 114 are collected on the filter 120 face. The sensor 150 may be part of the vacuum source 140 as shown in FIG. 1 or as a separate component.

Figure 2:
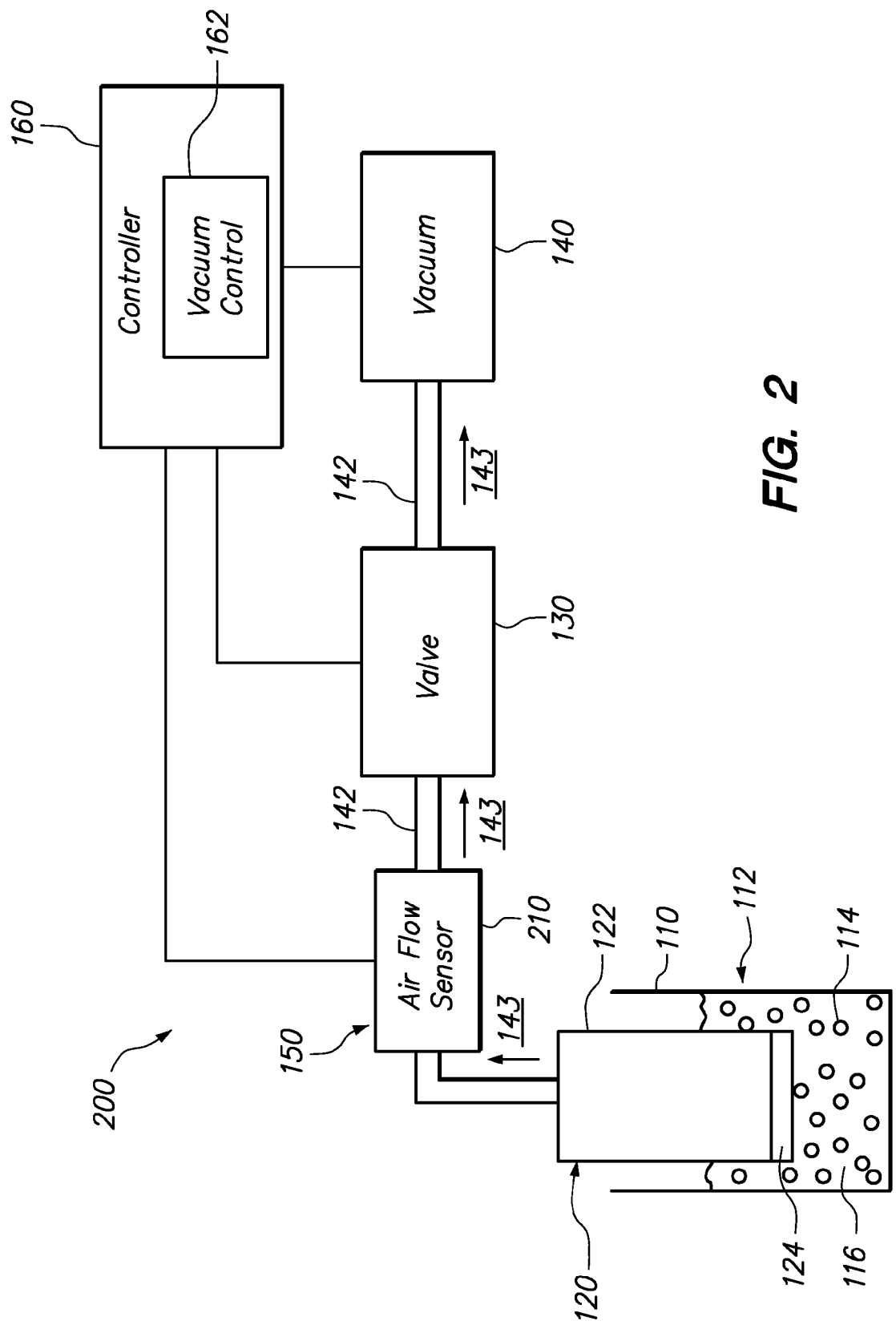
FIG. 2 is a block diagram of a system constructed according to another embodiment that is configured or operable to prepare a specimen slide while limiting the aspiration rates of specimen fluid and that determines filter coverage based on changes of air flow through a flow sensor.

Referring to FIG. 2, in a system 200 constructed according to another embodiment, the sensor 150 is an air sensor flow sensor 210 such as a mass air flow sensor that may be positioned between the filter 120 and the valve 130 or at other locations to detect the rate of air flow through the filter 120. The air flow rate is representative of the filter 120 coverage or percentage of the surface area of the filter 120 that is covered by cells 114 since the air flow decreases as more cells 114 are collected on the filter 120 face. For ease of explanation, reference is made to a sensor 150 generally, but it should be understood that different types of sensors 150 may be utilized including the sensors and sensor arrangements described in the references previously incorporated herein by reference and illustrated in FIGS. 1-2.

Figure 3:
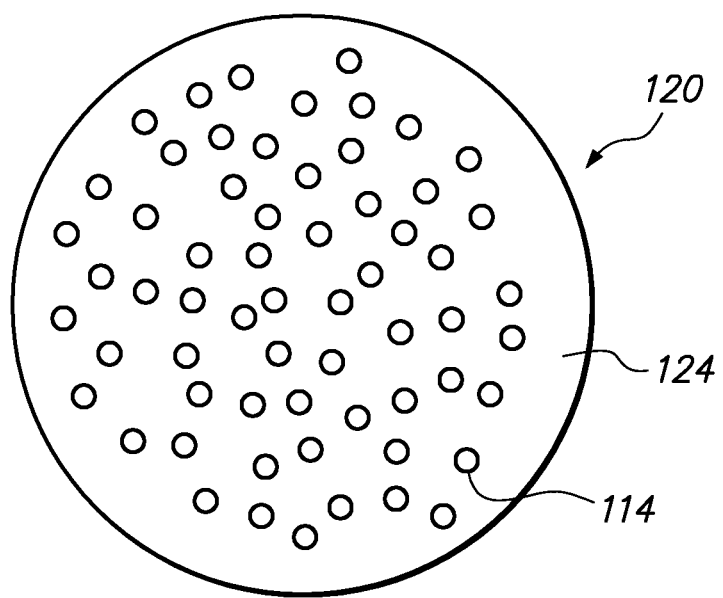
FIG. 3 is a bottom view of a face of a cytological filter for collecting cells to be applied to a specimen slide.

According to embodiments, the controller 160 is configured or operable, by software, hardware or a combination thereof, to determine a maximum rate of aspiration of the specimen fluid 116 across the filter element 124 and to further determine one or both of an amplitude and a duration of a vacuum applied by vacuum source 140 based at least in part upon the determined maximum rate of aspiration in order to control the amplitude and duration of the vacuum to govern the flow of specimen fluid 116 across the filter 120. In this manner, the amplitude and/or duration of the vacuum 143 and the flow of specimen fluid 116 are limited such that cells 114 can be controllably collected on the filter element 124 as shown in FIG. 3 and applied to a specimen slide 400 as shown in FIGS. 4-5 more quickly while providing the desired level of filter element 124 coverage, reducing or maintaining cell clustering compared to known specimen slide preparation systems and methods.

Figure 6A:
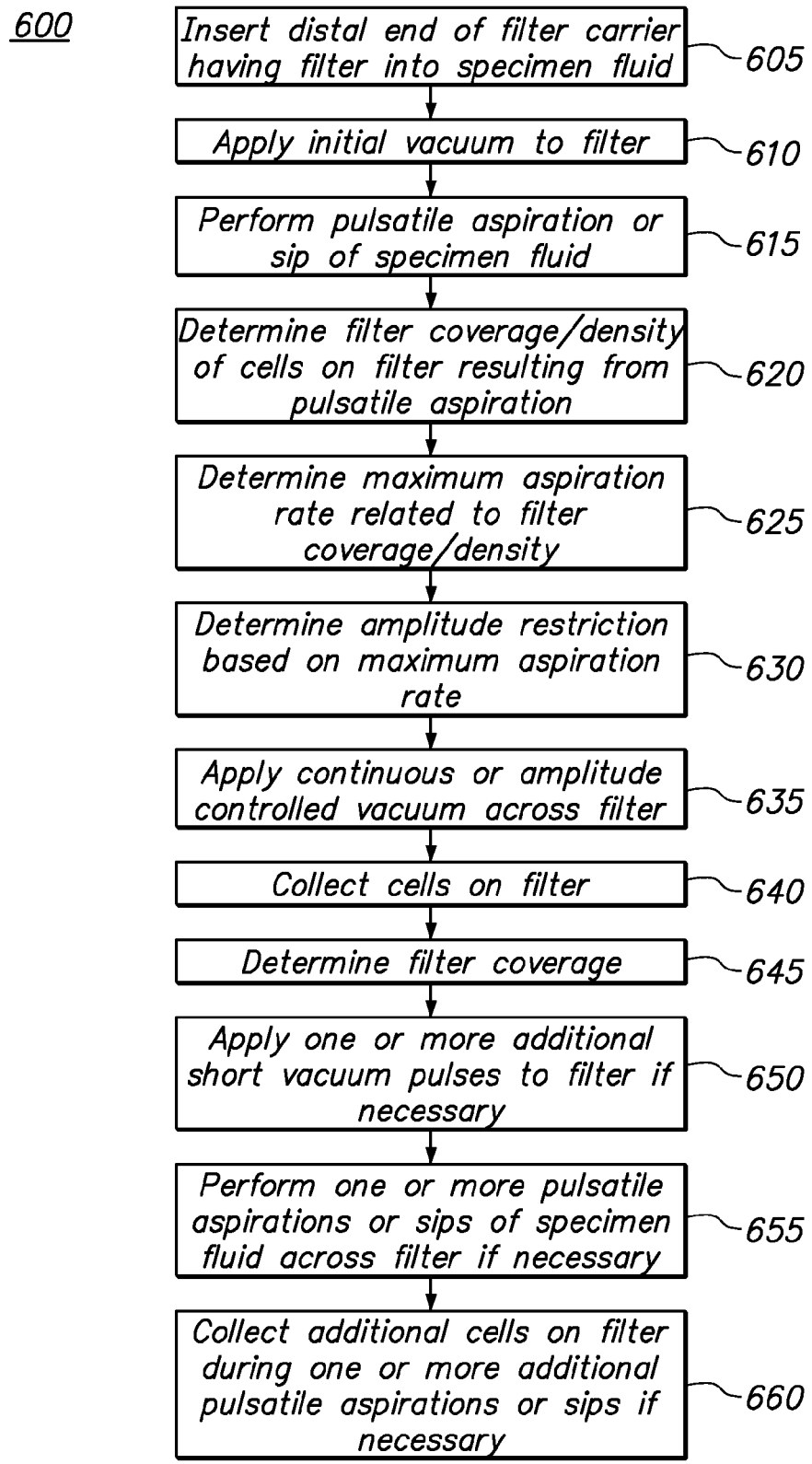
FIG. 6A is a flow diagram illustrate one embodiment of a method for preparing a specimen slide and that involves determining a maximum rate of aspiration of the specimen fluid across the filter and applying amplitude controlled vacuum across the filter to collect cells on the filter.
Figure 7:
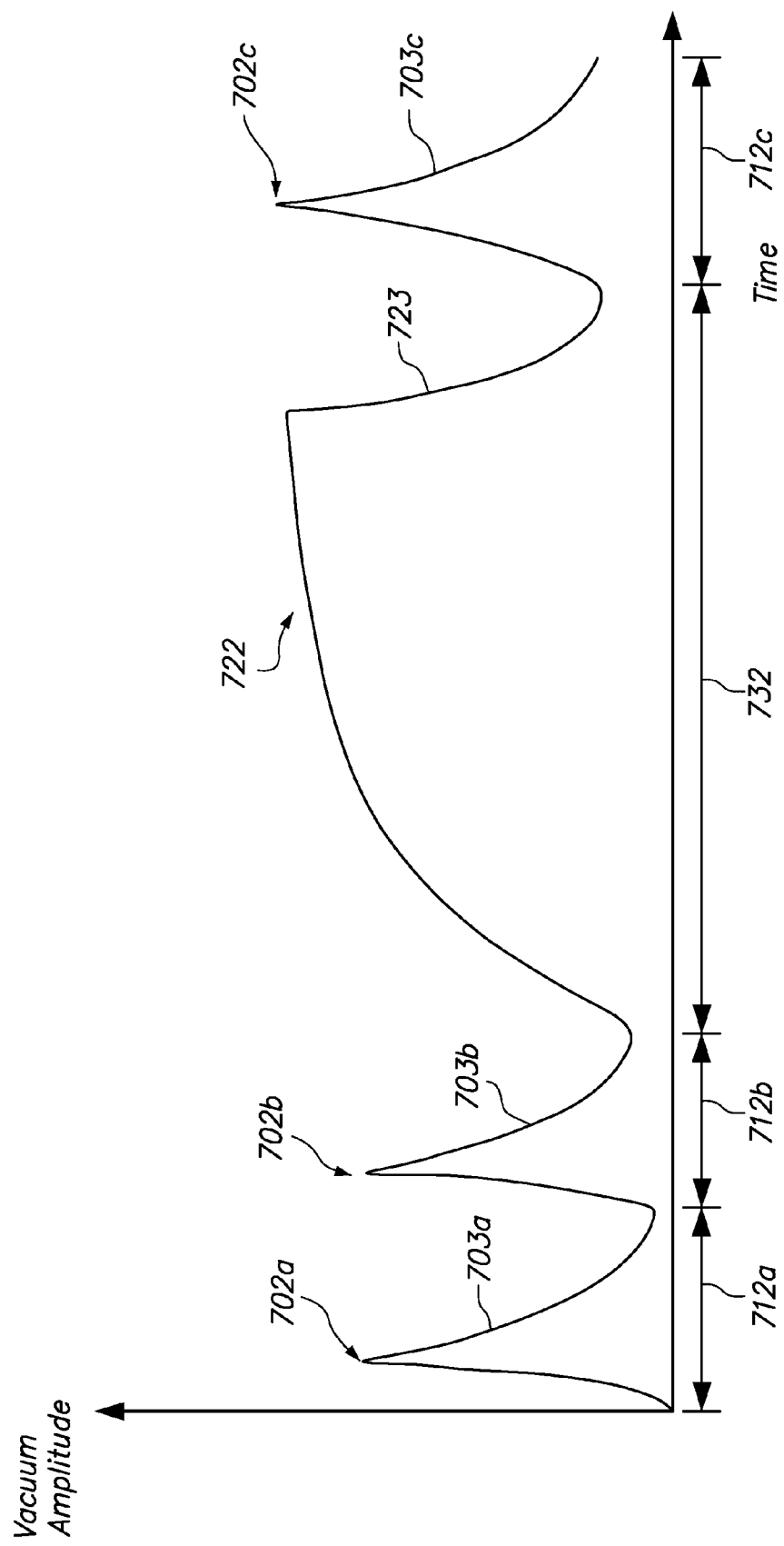
FIG. 7 is a graph of vacuum control according to one embodiment illustrating application of initial vacuum pulses to sip specimen, longer duration continuous aspiration to collect cells, and one or more optional vacuum pulses for one or more additional sips if additional filter coverage is necessary.

Referring to FIG. 6A, in one embodiment of a method 600 for preparing a specimen slide 400, a distal end of the filter 120 having the filter element or membrane 124 is inserted into the specimen fluid 116 at stage 605. As shown in FIG. 1, the other end of the filter 120 is coupled to the vacuum chamber 140 through the valve 130 and vacuum conduits 142. At stage 610, and with further reference to FIG. 7, one or more short vacuum pulses 702 (two pulses 702a and 702b are shown in FIG. 7) are applied to the filter 120 by opening and closing the valve 130 to apply short pulses of vacuum 142 to the filter 120 which, in turn, results in pulsatile aspirations or "sips" 712 of specimen fluid 116 from the vial 110 (two pulsatile aspirations 712a and 712b are shown in FIG. 7) and up into the filter 120 at stage 615. While FIG. 7 illustrates two short vacuum pulses 702a and 702b and corresponding pulsatile aspirations 712a and 712b of specimen fluid 116, embodiments may involve other numbers of vacuum pulses 702 and pulsatile aspirations 712.

More particularly, the valve 130 is opened to begin a pulsatile aspiration 712 with the vacuum source 140 applying a negative pressure pulse 702 to the interior of a cartridge 122 of the filter 120 such that the pressure inside the filter cartridge 122 is temporarily lowered. When a desired pressure change is detected by the sensor 150, the vacuum source 140 is deactivated by the controller 160. During each pulsatile aspiration 712, the pressure drop "decays" 703 (decays 703a and 703b are shown in FIG. 7) as the interior pressure equilibrates with the ambient pressure as the specimen fluid 116 is drawn across the membrane 124 to collect cells 114 on the filter membrane 124.

Referring again to FIG. 6A, at stage 620, in one embodiment, the decay 703 of this temporary pressure drop is detected by the sensor 150, and the change in pressure inside of the filter 120 over time detected by the sensor 150 is used to calculate the amount of cells 114 collected on the filter membrane 124 or the "membrane occlusion percentage". The vacuum level decays faster when the filter membrane 124 has no cells 114 or only a few cells 114 compared to when the filter membrane 124 has collected a larger number of cells 114.

As discussed above with reference to FIG. 2, an air flow sensor 210 may also be utilized for to determine filter coverage percentages based on changes in air flows rather than changes in vacuum decay. In embodiments utilizing a mass air flow sensor 210 (as shown in FIG. 2), the fluid flow rate is faster when the filter 120 has no cells 114 or only a few cells 114 compared to when the membrane 124 has collected a larger number of cells 114.

For this purpose, each filter 120 may be tested prior to processing to determine the initial baseline rate of vacuum decay when vacuum 140 is applied to the filter 120 to draw specimen fluid 116 that is free or substantially free of cells 114, and then subsequent decay rates are compared to the baseline rate. The rate at which the vacuum level decays from an initial level to a lower level is indicated by reading the sensor 150 over time. Sufficient membrane 124 coverage is determined to be obtained when the measured rate of vacuum decay drops below a threshold, e.g., a 20-30% reduction relative to the baseline vacuum decay rate.

If the desired or pre-determined level of filter coverage is already obtained as a result of the initial pulsatile aspirations 712, no further aspiration is required, and a specimen slide 400 can be prepared as shown in FIGS. 4-5. However, if the desired or pre-determined filter coverage was not obtained during the initial one or more pulsatile aspirations 712, then at stage 625, a maximum rate of aspiration of the specimen fluid 116 across the filter element 124 for additional collection of cells 114 is determined.

According to one embodiment, the maximum aspiration rate is based on or is related to the percentage of the surface area of the filter element 124 that is covered by cells 114. In one embodiment, the maximum rate of aspiration of specimen fluid 116 is empirically determined prior to preparation of specimen slides 400, i.e. prior to stages 605-620. In one embodiment, maximum aspiration rates may be based on prior tests or studies that correlate maximum aspiration rates of specimen fluid 116 and percentages of a filter element 124 that are covered with cells 116 while achieving acceptable levels of cell clustering in a sufficiently short amount of time to achieve desired throughput levels.

Figure 6B:
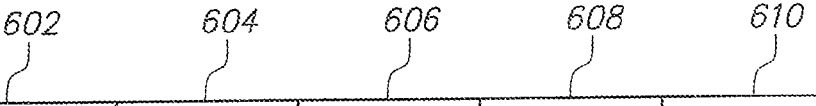
FIG. 6B illustrates a table including empirical test data that may be utilized by a controller and in the method shown in FIG. 6A.

For example, as shown in FIG. 6B, tests or studies performed prior to preparation of a specimen slide 400 may correlate maximum aspiration rates ("MAR" in first column 602) for a given filter coverage ("FC" in second column 604) that allowed for satisfactory levels of cell clustering ("CC" in third column 606) in a certain amount of time ("T" fourth column 608), and the amplitude, e.g., a maximum amplitude or amplitude limitation ("MA" in fifth column 610) of vacuum that was used to achieve these results. It should be understood that some or all of these criteria may be utilized for empirical testing, and that other criteria, models, simulations and methodologies may be utilized to determine maximum aspiration rates. Thus, FIG. 6B is provided as one example of how maximum aspiration rates may be determined.

For example, according to another embodiment, the maximum aspiration rate is based on or related to a cellular density of the cytological specimen 112. In one embodiment, rather than performing tests involving filter coverage, an energy source such as a laser or ultrasound source, is positioned to direct energy towards the cytological specimen 112 within the vial 110. A sensor is arranged to detect energy that is reflected from the specimen 112. Reflected energy is indicative of the cellular density of the cytological specimen 112. Thus, in these embodiments, the column related to filter coverage in column 604 may be replaced by data relating to reflections or cellular densities as determined utilizing transmitted and reflected energy. Other embodiments may involve both filter coverage data (as shown in FIG. 6B) and reflection or cellular density data. For ease of explanation, reference is made to empirically determined maximum aspiration rates based on percentages of filter elements 124 that are covered by cells 116 (e.g., using pulsatile aspiration and vacuum decay or air flow changes), but it should be understood that embodiments may involve other methods and techniques to determine maximum aspiration rates, which may or may not involve filter coverage.

Figure 6C:
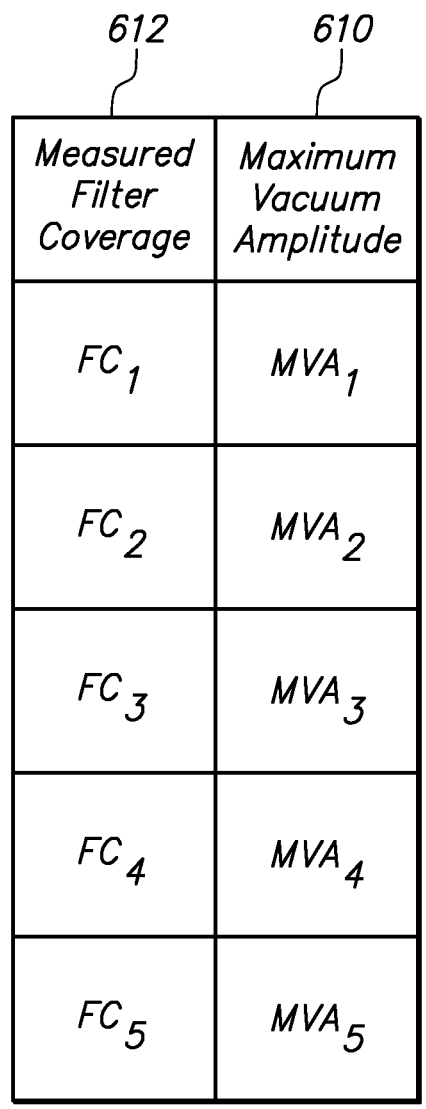
FIG. 6C illustrates a table that correlates filter coverage detected or determined during preparation of a specimen slide and a corresponding vacuum amplitude limitation or control.

Referring again to FIG. 6A and with further reference to FIG. 6C, during processing of a cytological specimen 112, at stage 630, an amplitude limitation or maximum vacuum amplitude (MVA) of continuous or amplitude controlled vacuum that is to be subsequently applied to collect cells 114 following the initial application of vacuum or pulsatile aspirations 712 is determined based at least in part upon the maximum aspiration rate. In the illustrated embodiment, the MVA is based on the maximum rate of aspiration of specimen fluid 116, which is based on, or related to, a measured or determined filter coverage, as shown in FIG. 6C. For this purpose, as shown in FIG. 6C, the controller 160 receives, reads or derives the cell coverage data from the sensor 150, locates the filter coverage in the table (column 612) and determines a corresponding MVA (column 610) to effectuate a limit on the aspiration rate of specimen fluid 116 according to the empirically determined data in FIG. 6B.

At stage 635, and as shown in FIG. 7, a continuous, amplitude-limited vacuum 722 having a duration that is substantially longer than the vacuum pulse 702 is applied to or across the filter 120, thereby resulting in aspiration of specimen fluid 116 having a duration that is substantially longer than a pulsatile aspiration 702 of specimen fluid 116. The continuous vacuum 722, however, is limited and controlled based at least in part upon the determined MVA such that the maximum aspiration rate is not exceeded. For example, the amplitude of the continuous vacuum 722 may be set at or below, or limited to, the determined MVA.

At stage 640, cells 114 are collected on the filter membrane 124 during the longer duration, aspiration 732 of specimen fluid 116 as a result of the longer duration, continuous vacuum 722. At stage 645, the percentage or portion of the surface area of the filter 120 that is covered by cells 114 following continuous vacuum 722 is determined, e.g., using one or more subsequent sips (one sip 702c is shown) and monitoring vacuum decay 703c as discussed above. If necessary, at stage 650, one or more additional short vacuum pulses 702 are applied across the filter 120 such that at stage 655, one or more additional pulsatile aspirations or sips 712 of specimen fluid 116 are performed, and additional cells 114 are collected on the filter membrane 124 during the vacuum pulse 702 at stage 660 if additional cell coverage is necessary. In some embodiments, the method 600 ends with the continuous vacuum 722 and longer duration aspiration 732, but in other embodiments, additional follow-up pulses 702 and pulsatile aspirations 712 are performed to fine tune the filter coverage if slightly more coverage is needed or desired.

Figure 8A:
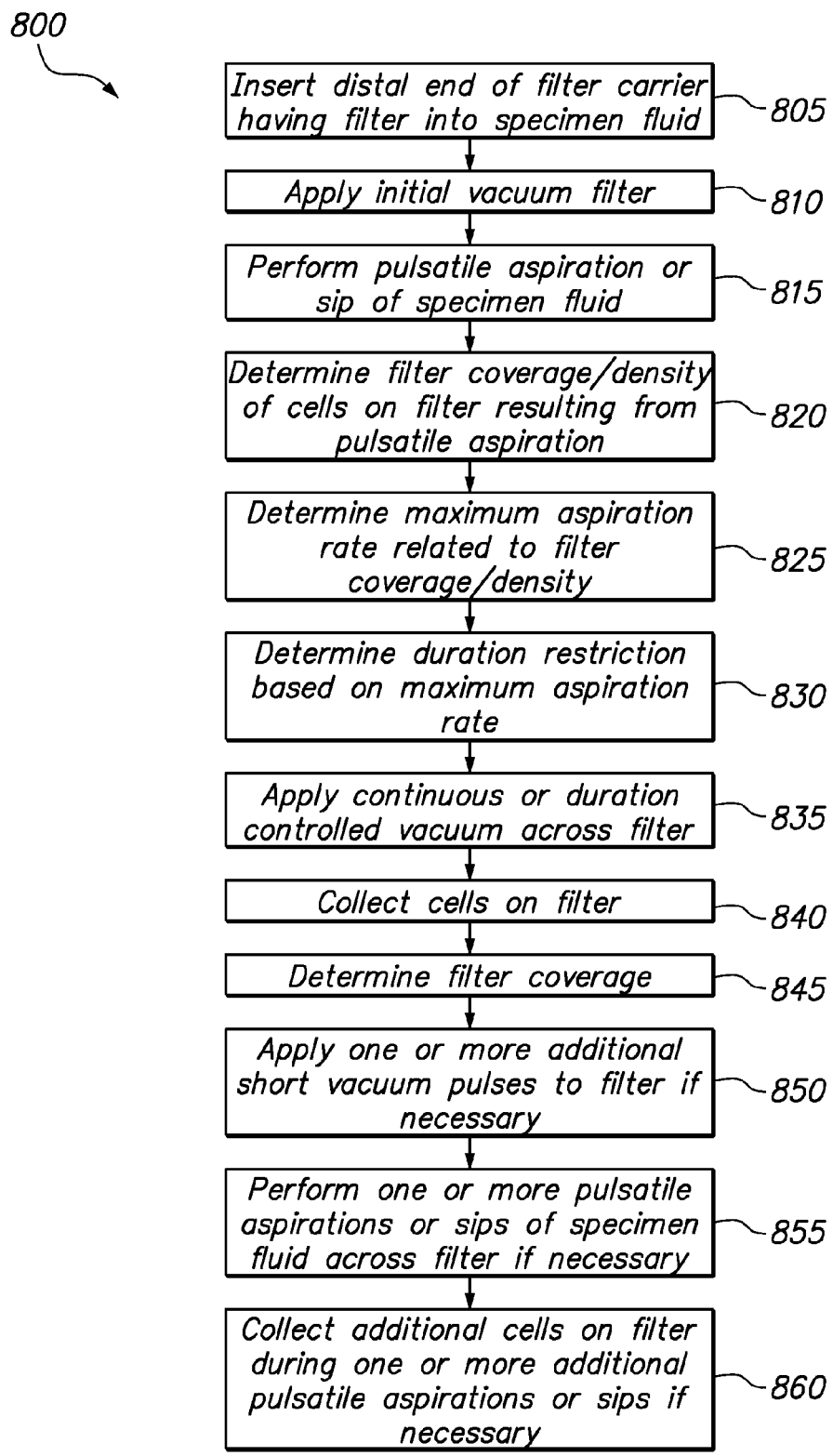
FIG. 8A is a flow diagram illustrate one embodiment of a method for preparing a specimen slide and that involves determining a maximum rate of aspiration of the specimen fluid across the filter and applying duration controlled vacuum across the filter to collect cells on the filter.
Figure 8B:
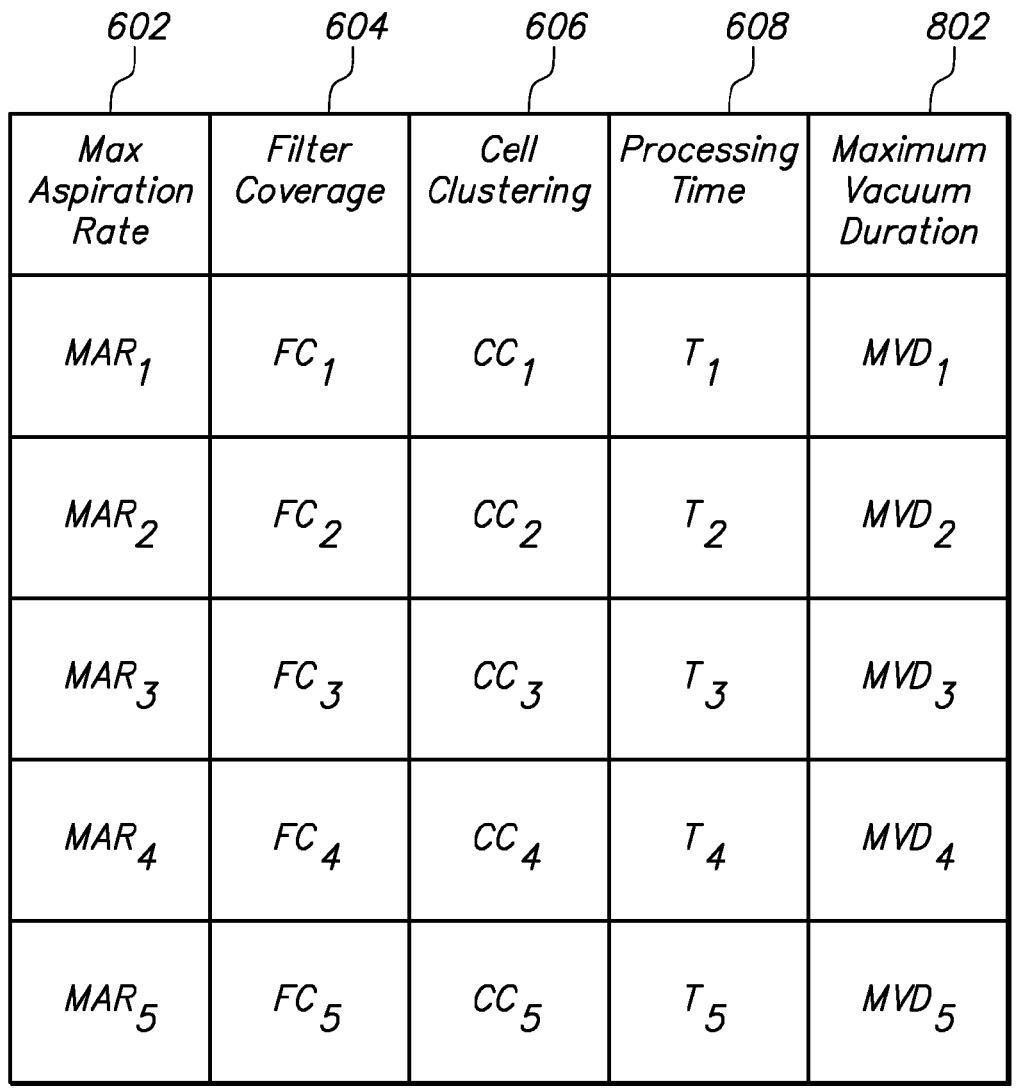
FIG. 8B illustrates a table including empirical test data that may be utilized by a controller and in the method shown in FIG. 8A.
Figure 8C:
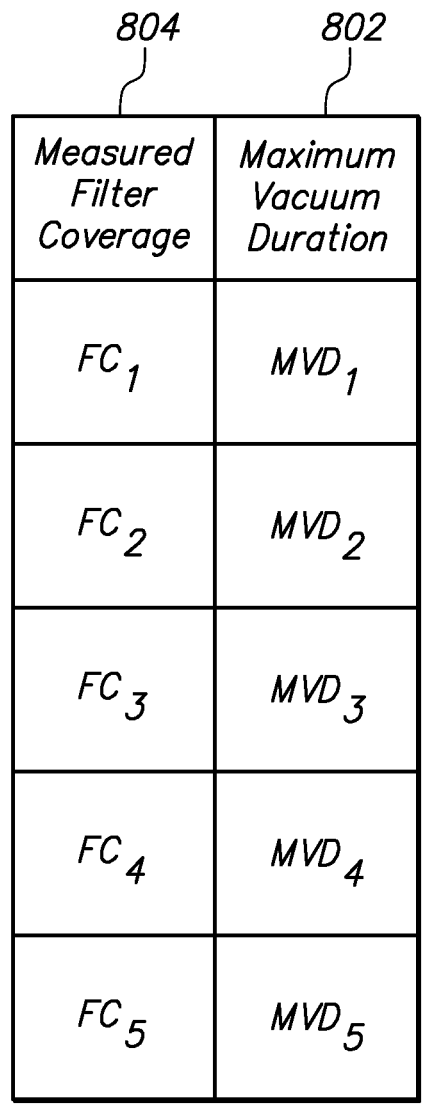
FIG. 8C illustrates a table that correlates filter coverage detected or determined during preparation of a specimen slide and a corresponding vacuum duration limitation or control.

Referring to FIGS. 8A-C, in another embodiment of a method 800 for preparing a specimen slide 400, a distal end of the filter 120 having the filter element or membrane 124 is inserted into the specimen fluid 116 at stage 805, one or more short vacuum pulses 702 are applied to the filter 120 at stage 810 which, in turn, results in pulsatile aspirations or "sips" 712 of specimen fluid 116 from the vial 110 at stage 815. At stage 820, in one embodiment, the decay 703 of this temporary pressure drop is detected by the sensor 150, and the change in pressure inside of the filter 120 over time detected by the sensor 150 is used to calculate the amount of cells 114 collected on the filter membrane 124. As discussed above with reference to FIG. 2, an air flow sensor 210 may also be utilized for this purpose. If the desired or pre-determined level of filter coverage is already obtained as a result of the initial pulsatile aspirations 712, no further aspiration is required, and a specimen slide 400 can be prepared as shown in FIGS. 4-5. However, if the desired or pre-determined filter coverage was not obtained during the initial one or more pulsatile aspirations 712, then at stage 825, a maximum rate of aspiration of the specimen fluid 116 across the filter element 124 for additional collection of cells 114 is determined.

According to one embodiment, as discussed with reference to FIGS. 6A-C, the maximum aspiration rate is based on, or related to, the percentage or portion of the filter element 124 surface area that is covered by cells 114 and may be empirically determined prior to preparation of specimen slides 400. In one embodiment, maximum aspiration rates may be based on prior tests or studies that correlate maximum aspiration rates of specimen fluid 116 and percentages or portions of a filter element 124 that are covered with cells 116 while achieving acceptable levels of cell clustering in a sufficiently short amount of time to achieve desired throughput levels.

For example, as shown in FIG. 8B, tests or studies performed prior to preparation of a specimen slide 400 may correlate maximum aspiration rates (first column 602) for a given filter coverage (second column 604) that allowed for satisfactory levels of cell clustering (third column 606) in a certain amount of time (fourth column 608), and the duration, e.g., a maximum vacuum duration or duration limitation ("MVD" in column 802) of vacuum that was used to achieve these results. It should be understood that some or all of these criteria may be utilized for empirical testing, and that other criteria, models, simulations and methodologies may be utilized to determine maximum aspiration rates. Thus, FIG. 8B is provided as one example of how maximum aspiration rates may be determined. For example, as discussed with reference to FIGS. 6A-C, the maximum aspiration rate may also be based on or related to a cellular density of the cytological specimen 112, e.g., as determined utilizing an energy source and energy reflected from the cytological specimen 112. Other embodiments may involve both filter coverage data (as shown in FIG. 8B) and reflection or cellular density data.

Referring again to FIG. 8A, during processing of a cytological specimen 112, and with further reference to FIG. 8C, at stage 630, an amplitude limitation or maximum vacuum duration (MVD) of continuous or amplitude controlled vacuum that is to be subsequently applied to collect cells 114 following the initial application of vacuum or pulsatile aspirations 712 is determined based at least in part upon the maximum aspiration rate. In the illustrated embodiment, the MVD is based on the maximum rate of aspiration of specimen fluid 116, which is based on, or related to, a measured or determined filter coverage. For this purpose, as shown in FIG. 8C, the controller 160 receives, reads or derives the cell coverage data from the sensor 150, locates the filter coverage in the table (column 804) and determines a corresponding MVD (column 804) to effectuate a limit on the aspiration rate of specimen fluid 116.

At stage 835, a continuous, amplitude-limited vacuum 722 having a duration that is substantially longer than the vacuum pulse 702 is applied to or across the filter 120, thereby resulting in aspiration of specimen fluid 116 having a duration that is substantially longer than a pulsatile aspiration 702 of specimen fluid 116. The duration of the continuous vacuum 722, however, is limited and controlled based at least in part upon the determined MVD such that the maximum aspiration rate is not exceeded. For example, the duration of the continuous vacuum 722 may be set at or below, or limited to, the determined maximum vacuum duration.

At stage 840, cells 114 are collected on the filter membrane 124 during the longer duration, aspiration 732 of specimen fluid 116, and at stage 845, the percentage or portion of the surface area of the filter 120 that is covered by cells 114 following continuous vacuum 722 is determined. If necessary, at stage 850, one or more additional short vacuum pulses 702 are applied across the filter 120 such that at stage 855, one or more additional pulsatile aspirations or sips 712 of specimen fluid 116 are performed, and additional cells 114 are collected on the filter membrane 124 during the vacuum pulse 702 at stage 860 if additional cell coverage is necessary. In some embodiments, the method 800 ends with the continuous vacuum 722 and longer duration aspiration 732, but in other embodiments, additional follow-up pulses 702 and pulsatile aspirations 712 are performed to fine tune the filter coverage if slightly more coverage is needed or desired.

FIGS. 6A-C and 8A-C illustrate embodiments involving one constraint or limitation upon the continuous vacuum 722. However, in other embodiments, multiple constraints may be placed upon the continuous vacuum 722, which is particularly use for processing slides with acceptable cell clustering while increasing slide processing speeds or throughput. Thus, embodiments that control both vacuum amplitude and duration are able to provide a controllable a balance between specimen quality (degree of cell clustering) and processing speed or throughput. This is in contrast to certain known systems and methods that may attempt to increase throughput by applying higher levels of vacuum but with the negative result of excessive clustering or poor quality specimen slides. Thus, in certain known systems, increasing vacuum may actually cause specimen quality issues that require more time to resolve. However, embodiments address these issues by determining a maximum rate of aspiration of the specimen fluid across the filter and determining an amplitude and a duration of a vacuum based at least in part upon the determined maximum rate of aspiration in order to achieve a balance between specimen quality and processing speed. Further, embodiments provide for increased processing speed while maintaining specimen quality.

Figure 9A:
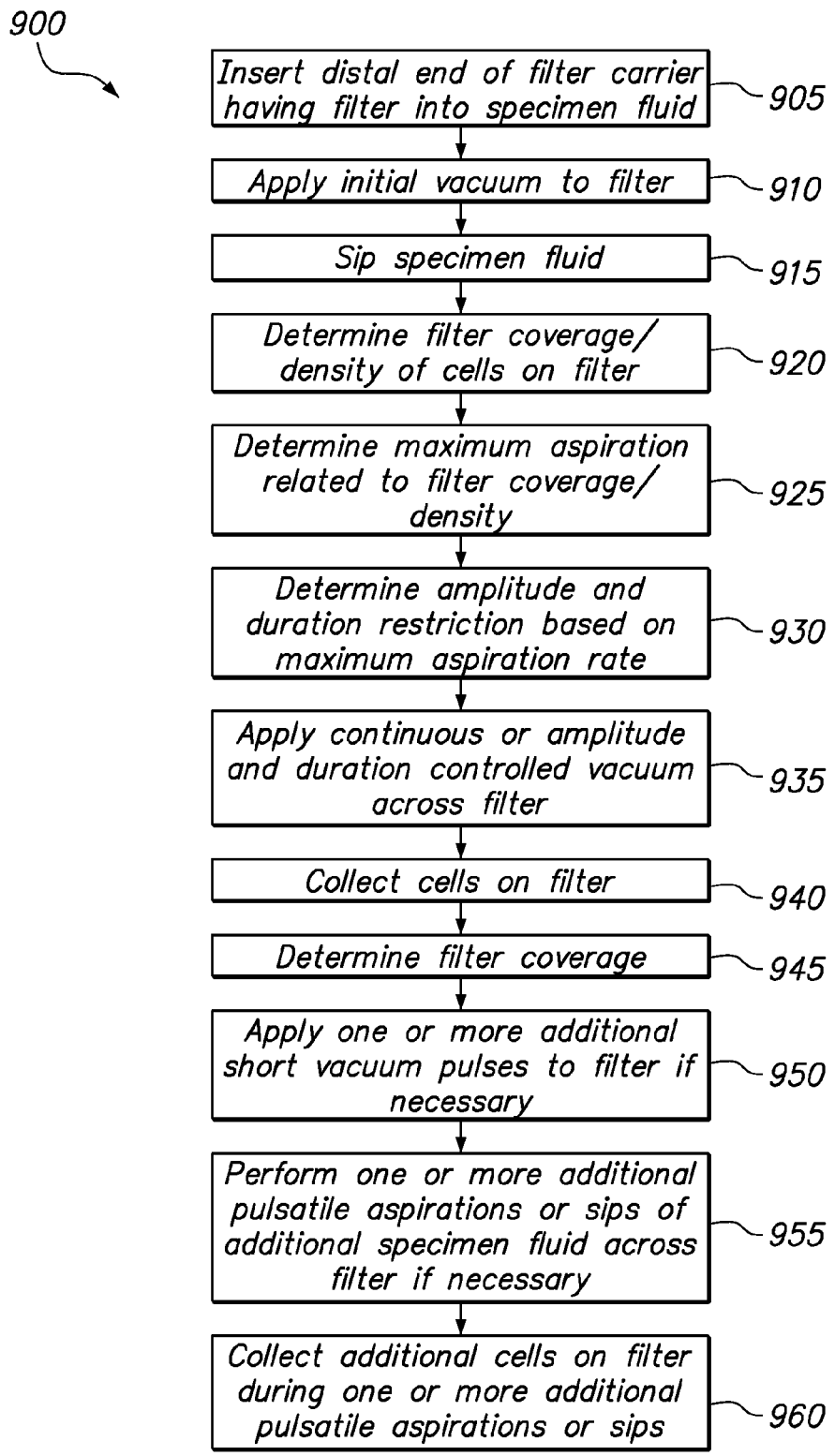
FIG. 9A is a flow diagram that illustrates one embodiment of a method for preparing a specimen slide and that involves determining a maximum rate of aspiration of the specimen fluid across the filter and applying amplitude and duration controlled vacuum across the filter to collect cells on the filter.
Figure 9B:
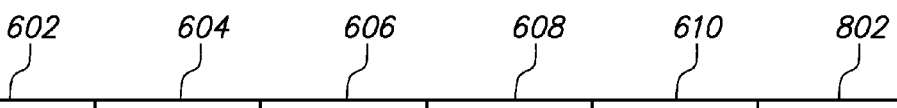
FIG. 9B illustrates a table including empirical test data that may be utilized by a controller and in the method shown in FIG. 9A.
Figure 9C:
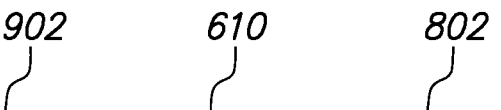
FIG. 9C illustrates a table that correlates filter coverage detected or determined during preparation of a specimen slide and corresponding vacuum amplitude and duration limitations or controls.

More particularly, referring to FIGS. 9A-C, in another embodiment of a method 900 for preparing a specimen slide 400, a distal end of the filter 120 having the filter element or membrane 124 is inserted into the specimen fluid 116 at stage 905, one or more short vacuum pulses 702 are applied to the filter 120 at stage 910 which, in turn, results in pulsatile aspirations or "sips" 712 of specimen fluid 116 from the vial 110 at stage 915. At stage 920, in one embodiment, the decay 703 of this temporary pressure drop is detected by the sensor 150, and the change in pressure inside of the filter 120 over time detected by the sensor 150 is used to calculate the amount of cells 114 collected on the filter membrane 124. As discussed above, an air flow sensor 210 may also be utilized for this purpose. If the desired or pre-determined level of filter coverage is already obtained as a result of the initial pulsatile aspirations 712, no further aspiration is required, and a specimen slide 400 can be prepared as shown in FIGS. 4-5. However, if the desired or pre-determined filter coverage was not obtained during the initial one or more pulsatile aspirations 712, then at stage 925, a maximum rate of aspiration of the specimen fluid 116 across the filter element 124 for additional collection of cells 114 is determined.

According to one embodiment, as discussed with reference to FIGS. 6A-C and FIGS. 8A-C, the maximum aspiration rate is based on, or related to, the percentage or portion of the surface area of the filter element 124 that is covered by cells 114 and may be empirically determined prior to preparation of specimen slides 400. For example, as shown in FIG. 9B, tests or studies performed prior to preparation of a specimen slide 400 may correlate maximum aspiration rates (first column 602) for a given filter coverage (second column 604) that allowed for satisfactory levels of cell clustering (third column 606) in a certain amount of time (fourth column 608), and amplitude, e.g., a maximum vacuum amplitude or amplitude limitation ("MVA" in column 610) and a duration, e.g., a maximum vacuum duration or duration limitation ("MVD" in column 802) of vacuum that was used to achieve these results. As discussed above, some or all of these criteria may be utilized for empirical testing, and that other criteria, models, simulations and methodologies may be utilized to determine maximum aspiration rates. Further, the maximum aspiration rate may also be based on or related to a cellular density of the cytological specimen 112, e.g., as determined utilizing an energy source and energy reflected from the cytological specimen 112. Other embodiments may involve both filter coverage data (as shown in FIG. 8B) and reflection or cellular density data. Thus, FIG. 9B is provided as one example of how maximum aspiration rates may be determined.

Referring again to FIG. 9A, during processing of a cytological specimen 112, and with further reference to FIG. 9C, at stage 930, vacuum amplitude and duration limitations are determined based at least in part upon the maximum aspiration rate. In the illustrated embodiment, the MVA and MVD are based on the maximum rate of aspiration of specimen fluid 116, which is based on, or related to, a measured or determined filter coverage. For this purpose, as shown in FIG. 9C, the controller 160 receives, reads or derives the cell coverage data from the sensor 150, locates the filter coverage percentage in the table (column 804) and determines a corresponding MVA (column 610) and MVD (column 802) to effectuate a limit on the aspiration rate of specimen fluid 116.

At stage 935, a continuous, amplitude-limited vacuum 722 having a duration that is substantially longer than the vacuum pulse 702 is applied to or across the filter 120, thereby resulting in aspiration of specimen fluid 116 having a duration that is substantially longer than a pulsatile aspiration 702 of specimen fluid 116. The duration of the continuous vacuum 722, however, is limited and controlled based at least in part upon the determined MVA and MVD such that the maximum aspiration rate is not exceeded. For example, the amplitude of the continuous vacuum 722 may be set at or below, or limited to, the determined maximum vacuum amplitude, and the duration of the continuous vacuum 722 may be set at or below, or limited to, the determined maximum vacuum duration.

At stage 940, cells 114 are collected on the filter membrane 124 during the longer duration, aspiration 732 of specimen fluid 116, and at stage 945, the percentage or portion of the surface area of the filter 120 that is covered by cells 114 following continuous vacuum 722 is determined. If necessary, at stage 950, one or more additional short vacuum pulses 702 are applied across the filter 120 such that at stage 955, one or more additional pulsatile aspirations or sips 712 of specimen fluid 116 are performed, and additional cells 114 are collected on the filter membrane 124 during the vacuum pulse 702 at stage 960 if additional cell coverage is necessary. In some embodiments, the method 900 ends with the continuous vacuum 722 and longer duration aspiration 732, but in other embodiments, additional follow-up pulses 702 and pulsatile aspirations 712 are performed to fine tune the filter coverage if slightly more coverage is needed or desired.

Figure 10:
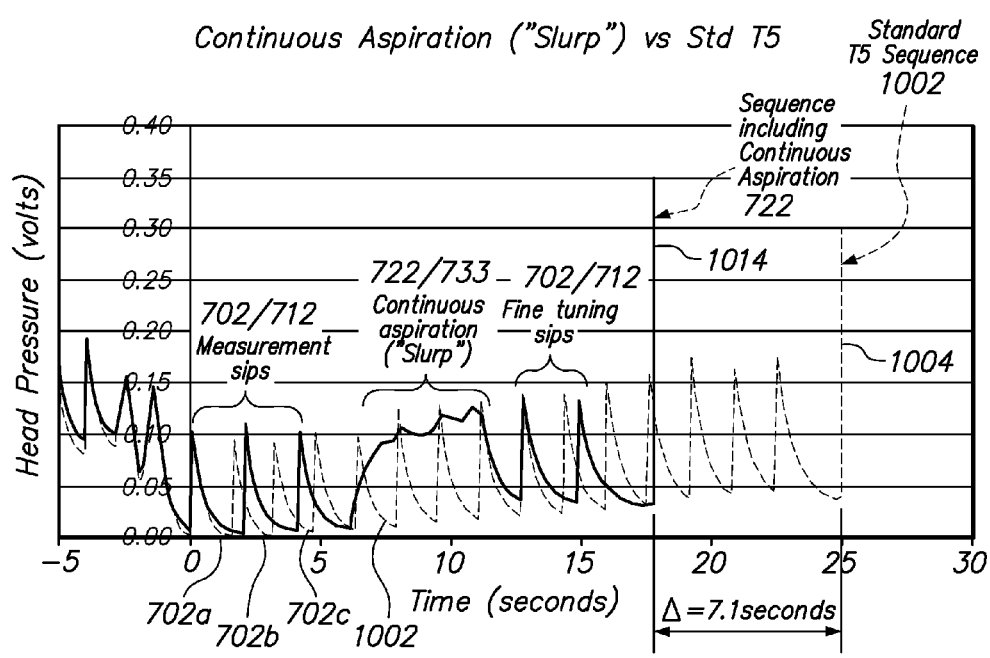
FIG. 10 is a graph of vacuum control according to one embodiment illustrating application of initial vacuum pulses to sip specimen, longer duration continuous aspiration to collect cells, and one or more optional vacuum pulses for one or more additional sips if additional filter coverage is necessary, compared to known sipping methods.

FIG. 10 illustrates in further detail vacuum control (shown in bold in FIG. 10) according to embodiments and compared to a series of pulsatile aspirations (shown in phantom in FIG. 10) used by a T5 slide processing system available from Hologic Corporation. As shown in FIG. 10, the T5 slide processing system utilizes a series of short vacuum pulses 1002 for performing a series of short measurement pulsatile aspirations. Sufficient cells (e.g., 30% filter coverage) are collected using the known system in about 25 seconds, at which point the filter is removed from the specimen fluid (as shown by vertical line 1004 at the end of the sequence).

With embodiments of the invention, however, short vacuum pulses 702 are applied to perform short initial pulsatile aspirations 712 of the specimen fluid 116, and these pulsatile aspirations 712 are followed by a longer duration, continuous and amplitude and/or duration controlled vacuum 722 for performing an extended duration, continuous aspiration or slurp 733 of the specimen fluid 116. A substantial majority, e.g., about 90-95%, of the cells 114 are collected on the filter membrane 124 during the extended duration aspiration 733. If necessary, one or more fine tuning vacuum pulses 702 and pulsatile aspirations 712 of specimen fluid 116 may be performed after the extended duration aspiration 733 before the filter 120 is removed from the specimen fluid 116 (as shown by line 1014) in order to add a small number of additional cells to the filter member 124.

According to one embodiment, the final pulsatile aspiration 702, e.g., the third pulsatile aspiration 702c in the example shown in FIG. 10 is selected as the pulsatile aspiration 702 that is used to determine filter coverage. This filter coverage is used to determine the amplitude and/or duration constraints on the continuous vacuum 722 to limit the aspiration rate during the continuous vacuum aspiration 733.

Further, in embodiments, the continuous vacuum 722 is applied without making any measurement or determination regarding filter coverage, i.e., the application of continuous vacuum 722 is blind. This is in contrast to the vacuum pulses 702 and pulsatile aspirations 712 during which cell coverage measurements or determinations are made. Thus, embodiments are able to perform dedicated cell collection during the continuous vacuum 722 without having to take cell coverage measurements, in contrast to known systems and methods in which measurements occur concurrently with a pulsatile aspiration.

As generally illustrated in FIG. 10, the duration of a vacuum pulse 702 and corresponding pulsatile aspiration 712 of the specimen fluid 116 may range from about one to two seconds as shown in FIG. 10, whereas the duration of the extended duration, continuous vacuum 722 and the corresponding extended duration, continuous aspiration 733 of specimen fluid 116 may be up to 60 seconds (or longer), for example, about five seconds as shown in FIG. 10. In certain embodiments, the durations of the continuous vacuum 722 and continuous aspiration 732 are substantially longer than durations pulses 702 and pulsatile aspirations 712, e.g., the durations of the vacuum 722 and continuous aspiration 732 are multiple times the duration of a pulse 702 and pulsatile aspiration 712. As such, and as shown by the area defined by the curves of a pulse 702/pulsatile aspiration 712 and the continuous vacuum 722/continuous aspiration 733, in certain embodiments, the amount of specimen fluid 116 flowing through the filter 120 during application of continuous vacuum 722 is substantially greater than the amount of specimen fluid 116 flowing through the filter 120 during a short vacuum pulse 702 and substantially greater than the amount of specimen fluid 116 flowing through the filter 120 during multiple short vacuum pulses 702.

The manner in which continuous vacuum 722 is applied for continuous aspiration 733 of specimen fluid 116 may vary. In certain embodiments illustrated in various figures a peak pulsatile pressure 702a is created by opening a QTO valve 130 to a tank at negative pressure for approximately 15-25 milliseconds and then quickly shutting the valve. The pulsatile pressure then decays 703a over approximately 1-1.5 seconds. The maximum pressure, as measured in volts by a head pressure sensor, ranges from 0.07 volts to 0.8 volts. The continuous vacuum 722 also has a maximum pressure, as measured in volts by a head pressure sensor, ranges from 0.07 volts to 0.8 volts. The duration of the continuous vacuum 722 is longer than the pulse and can have a duration of up to about 60 seconds (or longer), e.g., about 5 to about 60 seconds. The continuous pressure then decays 723 over approximately 1.5 second to 3 seconds. One or more additional pulses 702 of vacuum may be applied to the filter 120 after application of the continuous vacuum 722 until a desired level of coverage of cells 114 on the filter 120 is obtained, and these fine tuning pulsatile aspirations 712 may be similar to the initial pulsatile aspirations 702 described above.

Thus, as shown in FIGS. 7 and 10, embodiments that utilize an extended duration, continuous vacuum 722 for extended duration, continuous aspiration 732 of specimen fluid 116 collect a substantial majority of cells 114 to achieve the desired level of filter coverage more quickly than known systems and methods without impacting specimen quality. In the illustrated embodiment, use of the continuous vacuum 722 and aspiration 732 result in processing of a specimen slide 400 in about 18 seconds, or about 7 seconds faster than the known T2 slide processing system that utilizes only short vacuum pulses and pulsatile aspirations. Further, since embodiments restrict aspiration rates and vacuum amplitude and/or duration based on filter coverage and/or specimen density, embodiments are able to achieve these time savings while also accounting for different specimens having different cellular densities.

Figure 11A:
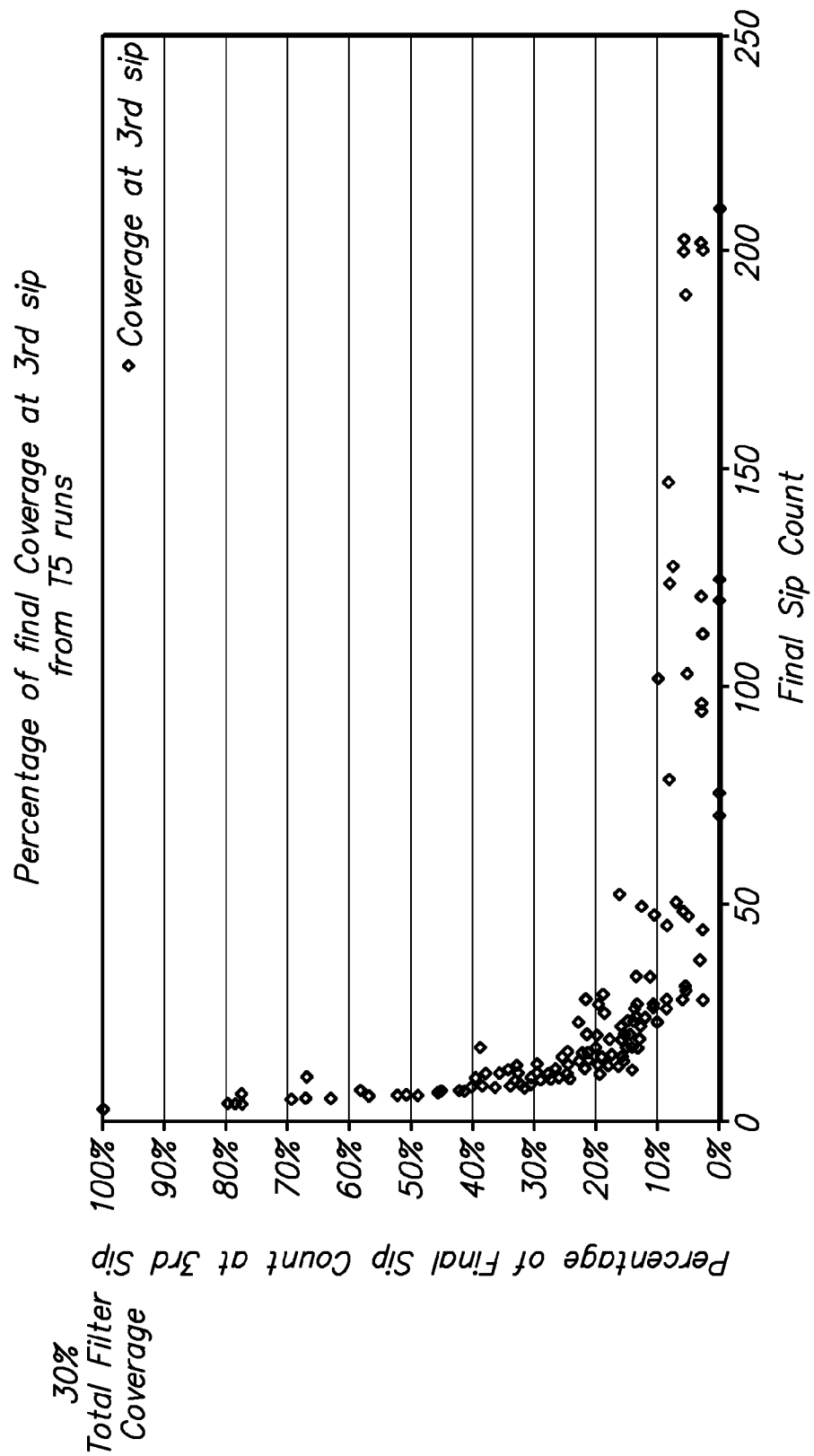
FIGS. 11A-C illustrate filter coverage data utilized for determining the amplitude and/or duration of a continuous vacuum to slurp specimen fluid according to one embodiment.
Figure 11B:
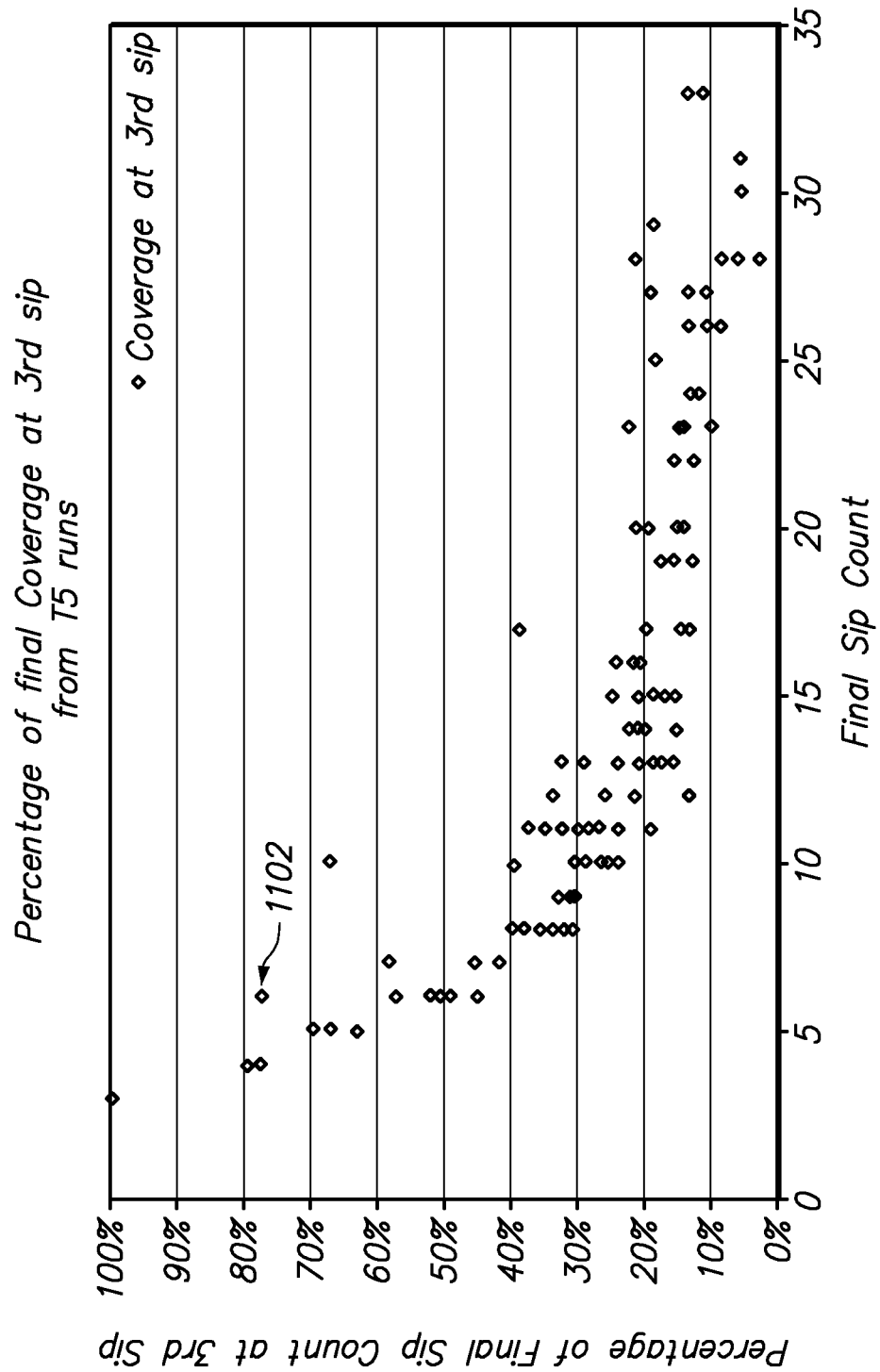

FIGS. 11A-B illustrate one method for determining the amplitude and/or duration of a continuous vacuum 722 as discussed above. These figures illustrate data acquired utilizing a known T5 specimen slide preparation system available from Hologic Corporation. In the illustrated example, three pulsatile aspirations were performed, and if a desired filter coverage level (e.g., 30%) is achieved, then aspiration is complete and a slide 400 is prepared. Otherwise, if the filter coverage is less than 30% during the first three pulsatile aspirations, then the filter coverage achieved during the third pulsatile aspiration is used to determine the amplitude and/or duration of the continuous vacuum 722 for continuous aspiration 732 of specimen fluid 116 according to embodiments.

FIG. 11A illustrates data collected during tests involving approximately 150 sample vials 110. The x-axis represents a number of pulsatile aspiration or "sips" (ranging from 0 to 250), and the y-axis represents a percentage of the desired filter level coverage on a third pulsatile aspiration (which occurs prior to continuous vacuum 722 and continuous aspiration 732 of specimen fluid 116). Thus, in the example in which the desired total filter coverage is 30%, this total filter coverage is represented as 100% on the y-axis, whereas 15% total filter coverage is represented as 50% on the y-axis.

FIG. 11A illustrates the percentage of Percent Coverage (30%) achieved on the third pulsatile aspiration (y-axis) versus the Final Sip Count or the number of pulsatile aspirations required to reach full coverage (x-axis). FIG. 11B illustrates the same data with the x-axis scale expanded to show the 0 to 35 range of pulsatile aspirations in greater detail. The data point 1102 at about 78% of the total desired coverage (or about 23.4% total coverage on the third pulsatile aspiration) and required a total of six pulsatile aspirations to reach the total desired filter coverage (30%). This data may then be utilized to determine the amplitude and/or duration of the continuous vacuum 722 according to embodiments as shown in FIG. 11C.

Figure 11C:
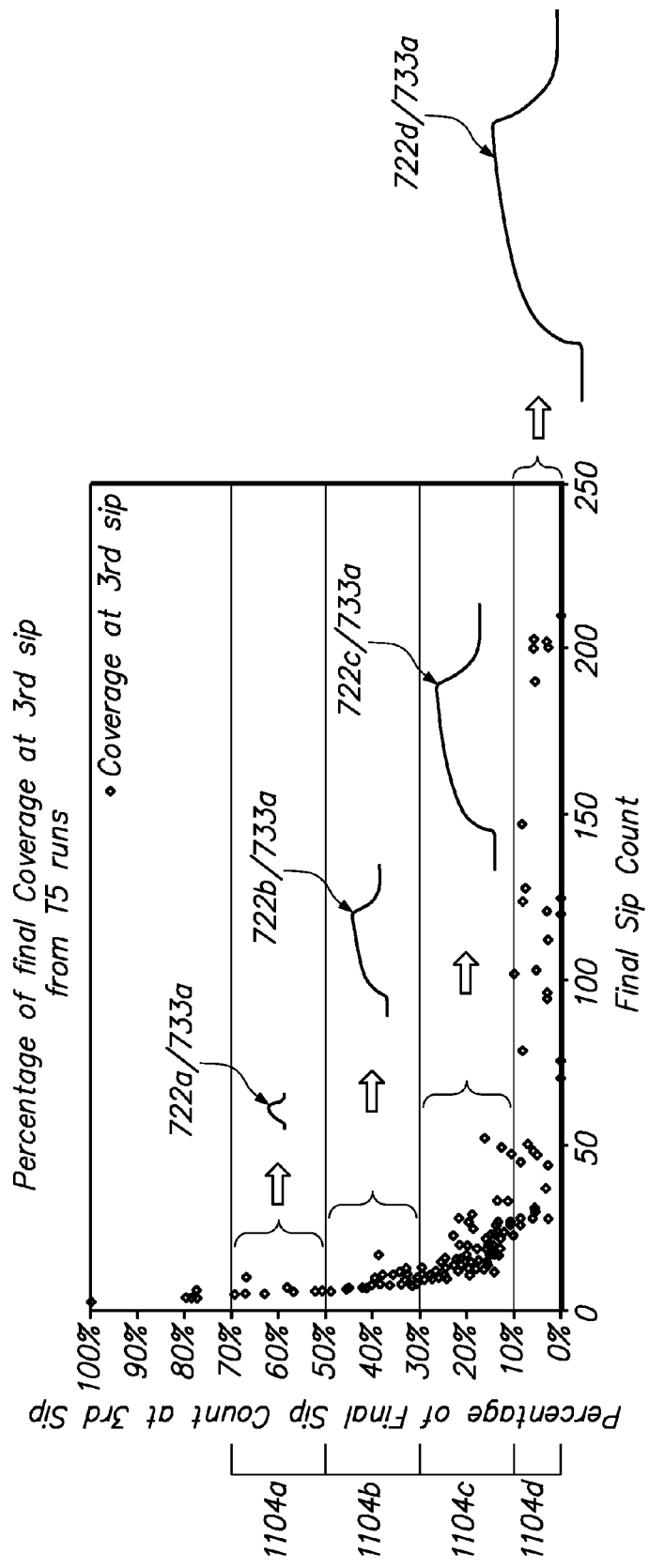

As shown in FIG. 11C, the continuous vacuum 722a for continuous aspiration 733a has the lowest amplitude and the shortest duration since this continuous vacuum 722a is applied to collect a smaller number of additional cells 114 in order to reach the total desired filter coverage (30%) given the cellular density of the specimen fluid 116, whereas continuous vacuum 722b has a higher amplitude and longer duration than continuous vacuum 722a to collect more cells 114 for less dense specimen fluid 116, continuous vacuum 722c has a higher amplitude and longer duration than continuous vacuum 722b to collect more cells 114 of even less dense specimen fluid 116, and continuous vacuum 722d has the highest amplitude and longest duration since specimens 722 to collect the most cells 114 since in this case, the specimen fluid 116 has the lowest cellular density. Further, there may be cases, e.g., with low density specimens 112, when extended duration, continuous aspiration 732 may need to be interrupted and measurement pulsatile aspirations 712 inserted therein to better estimate the duration of continuous aspiration 732 that is required.

One manner in which extended duration, continuous vacuum 722 may be formed to perform extended duration, continuous aspiration 733 of specimen fluid 116 is by opening the valve 130 and utilizing a regulated vacuum source or adjustable in-line pressure regulator that is connected to a source of negative pressure. It should be understood that various vacuum source and regulator components and configurations may be utilized for this purpose.

According to another embodiment, extended duration, continuous vacuum 722 may be formed to perform extended duration, continuous aspiration 733 by a series of very short pulses (e.g., having durations on the order of milliseconds as opposed to a pulse 702 and continuous vacuum 722 that are on the order of seconds). Thus, while the continuous vacuum 722 may be comprised of a train of very short, millisecond vacuum pulses, the durations of these millisecond pulses are sufficiently short such that the collectively form a continuous vacuum 722 for performing continuous aspiration 733 of specimen fluid 116. Thus, in these embodiments, the durations of the millisecond pulses that are used to form the continuous vacuum 722 are substantially less than the durations of pulses 702 of vacuum applied across the filter 120 for pulsatile aspiration 712 of specimen fluid 116 and substantially less than the durations of the continuous vacuum 722.

For example, according to one embodiment, pulses may be low duty cycle pulses (e.g. 1-15% duty cycle) having duration of about 3 to about 10 milliseconds, and a frequency of about 10 Hz, whereas the duration of the initial vacuum pulses 702 is on the order of seconds, and the duration of the continuous vacuum 722 may be multiple times the duration of a vacuum pulse 702.

Figure 12:
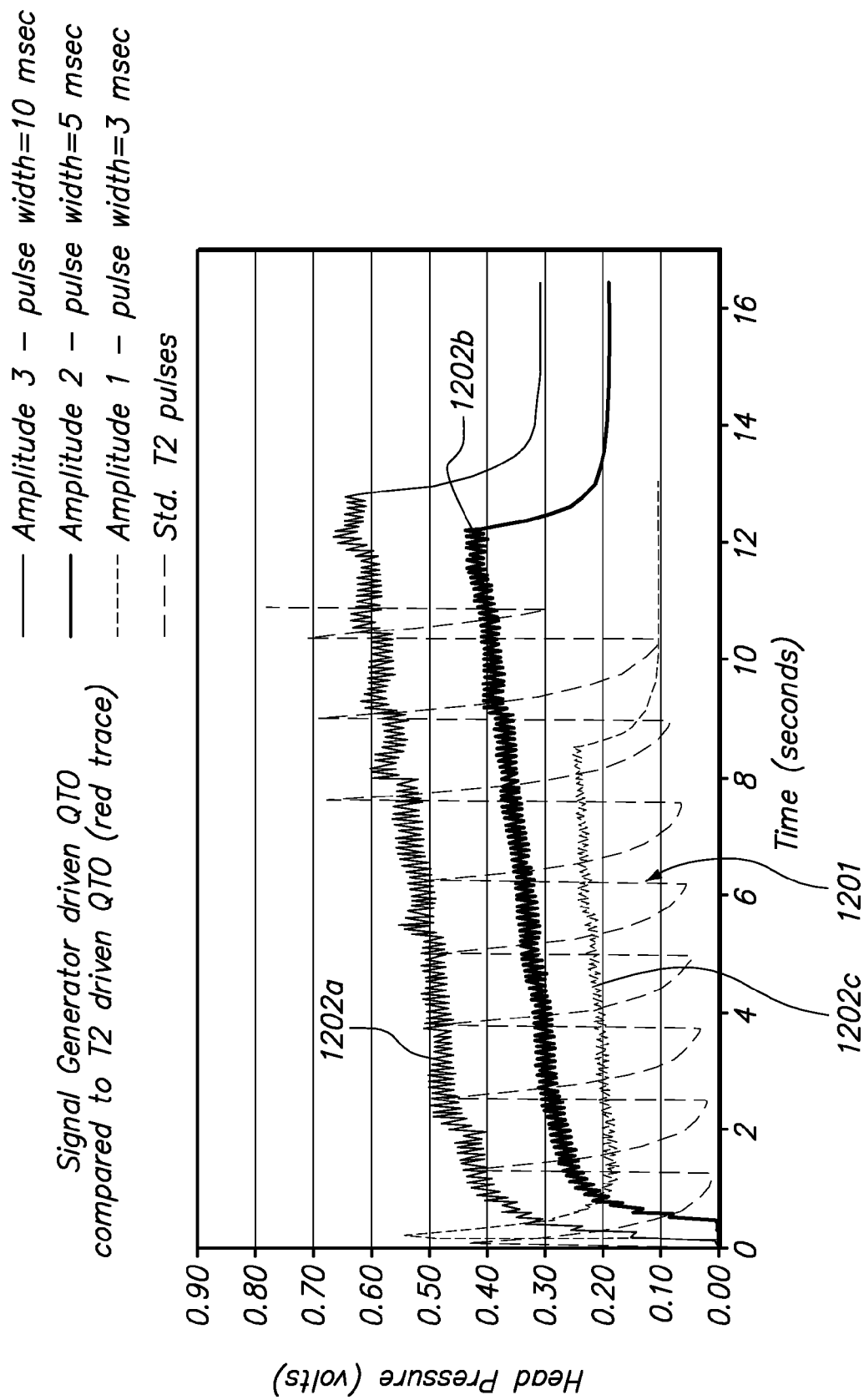
FIG. 12 is a graph illustrating three different applications of longer duration continuous vacuum formed by different pulse trains generated utilizing an external signal generator to slurp specimen according to embodiments.
Figure 13A:
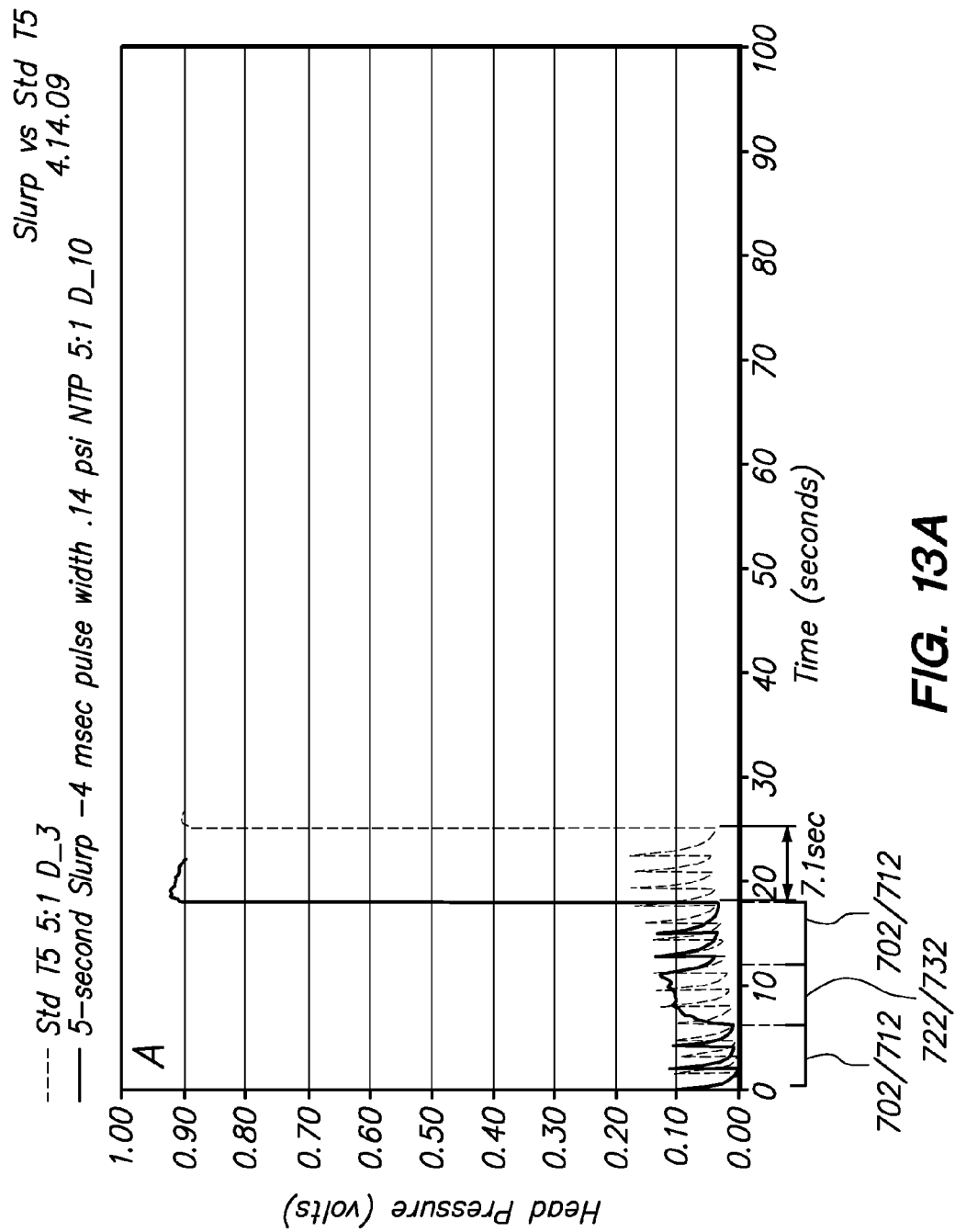
FIGS. 13A-D illustrate continuous vacuum and slurps having different durations and amplitudes.
Figure 13B:
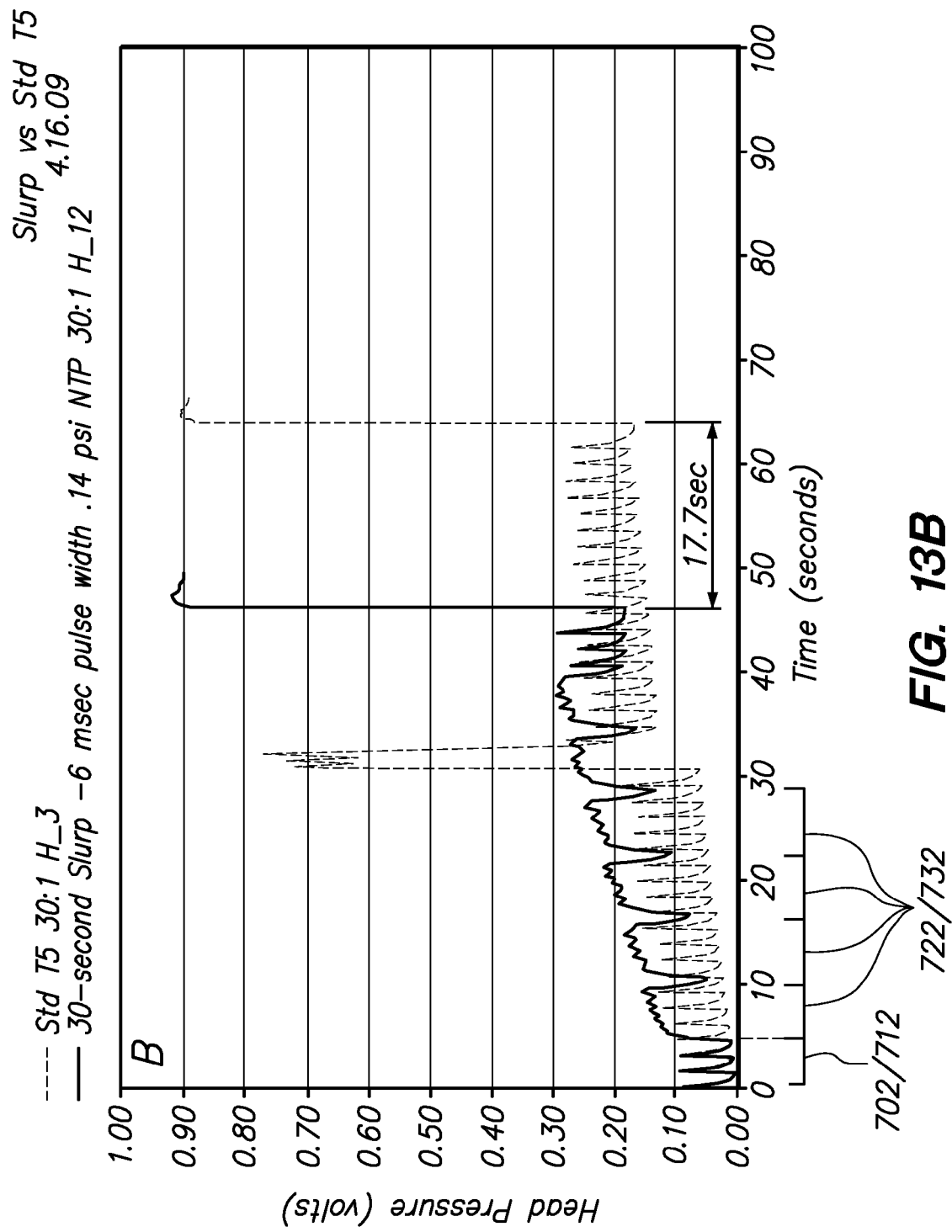
Figure 13C:
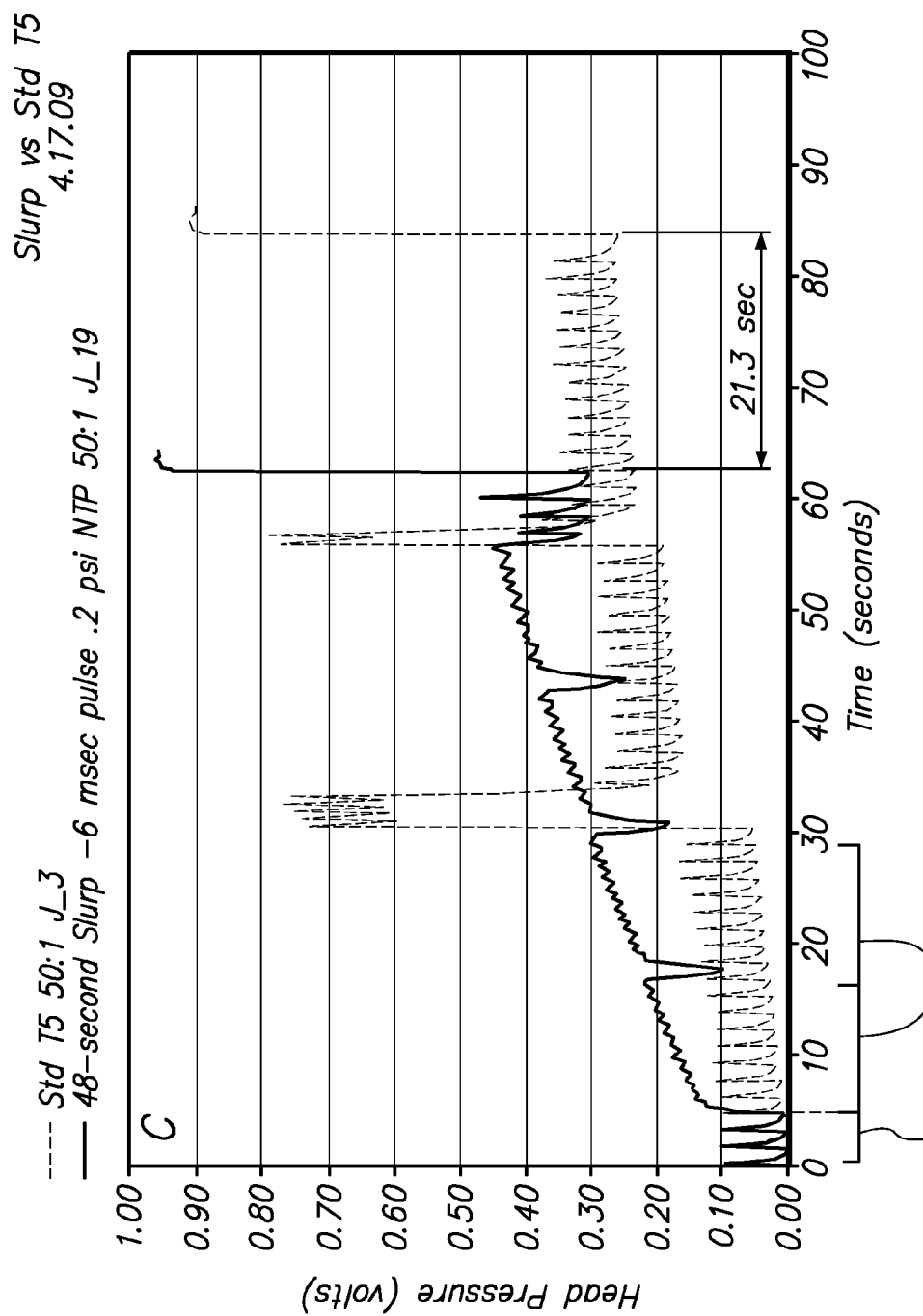
Figure 13D:
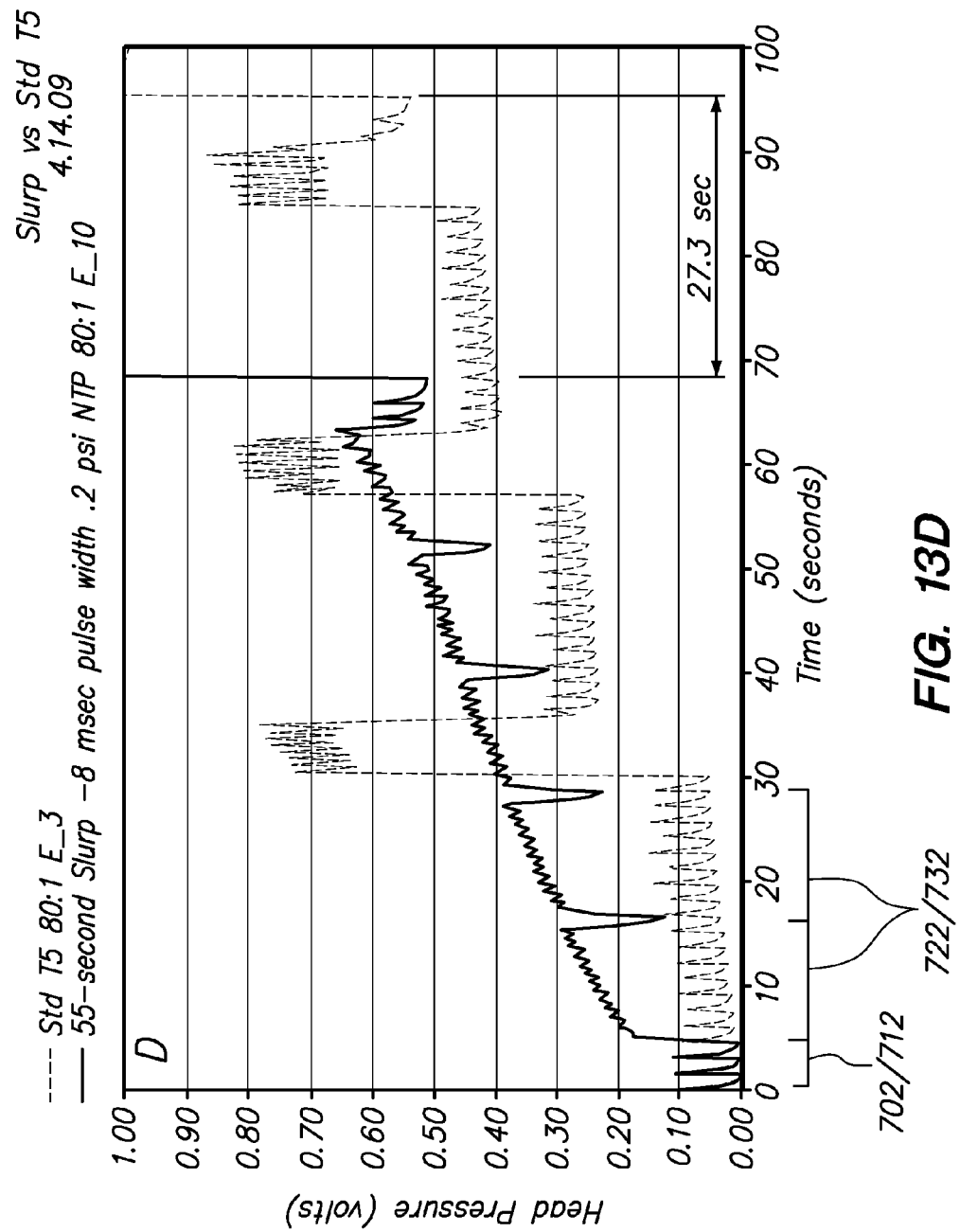

For example, FIG. 12 illustrates data acquired utilizing an external signal generator that was used to create a low duty cycle chain of pulses to modulate the QTO valve 130. In particular, FIG. 12 illustrates data collected by modulating the valve 130 with three duty cycle pulse chains and also illustrates sips (in phantom 1201) utilized by certain known systems and methods to illustrate the differences between embodiments and known systems and methods.

As shown in FIG. 12, the continuous vacuum 722 having the higher amplitude, Amplitude 3 (top trace 1202a), was created by applying a 10-volt 10 msec off and 90 msec on pulse train to QTO valve for approximately 13 seconds. In certain systems, the QTO valve 130 is open in the absence of any applied voltage and normally has a +12 volt signal applied to it to keep it closed. The continuous vacuum 722 having the next highest amplitude, Amplitude 2 (middle trace 1202b), was created by applying a 10-volt 5 msec off and 95 msec on pulse train to the QTO valve 130 for approximately 12 seconds. Continuous vacuum 722 having the lowest amplitude, Amplitude 1 (bottom trace 1202c) was created by applying a 10-volt 3 msec off and 97 msec on pulse train to QTO valve 130 for approximately 8.5 seconds.

Thus, an extended duration, continuous vacuum 722 and extended duration continuous aspiration 732 may be generated by opening the valve 130 and utilizing a regulated vacuum source or adjustable in-line pressure regulator that is connected to a source of negative pressure or by a pulse train such as externally generated low duty cycle pulse trains that are implemented by software and/or hardware in the controller 160 or other control or processing element of a slide processing system. Further, such systems may allow for various adjustable parameters including, for example, a number or a maximum number of continuous vacuum 722 applications or continuous aspirations 732, an initial number of vacuum pulses 702 and pulsatile aspirations 712 before a continuous vacuum 722 and continuous aspiration 732, a number of pulsatile aspirations between continuous aspirations 732 if multiple aspirations 732 are utilized, the time that the QTO valve 130 is open, the time that the QTO valve 130 is closed, the duration of the continuous vacuum 722, a delay after continuous aspiration 732 (milliseconds), and a number of continuous vacuum 722 applications and/or continuous aspirations 732.

Referring to FIGS. 13A-D and FIGS. 14A-B, to demonstrate the effectiveness of embodiments, parameters listed above were used to determine the maximum allowable duration and amplitudes of the continuous vacuum 722 to perform continuous aspiration 733 of specimen fluid 116. These maximum levels were determined experimentally by making slides 400 from four cell pools of different cellular densities using different vacuum amplitudes and durations. Control slides 400 were made with standard T5 processing system settings from the same cell pools and cell counts and cluster counts among slides were compared.

As shown in FIG. 13A-D, the durations of continuous aspirations 732 of specimen fluid 116 that were tested were 5 seconds, 30 seconds, 48 seconds and 55 seconds, and the respective amplitudes of these respective slurps were 0.11 volts, 0.28 volts, 0.43 volts and 0.63 volts. These continuous aspirations 732 were generated using pulse trains having respective pulse widths of 4 ms, 6 ms, 6 ms and 8 ms and respective vacuum levels of 0.14 psi, 0.14 psi, 0.20 psi and 0.20 psi. Data of these four test continuous aspirations 733 are shown in respective FIGS. 13A-D. Utilizing these tests aspirations 733 resulted in realized processing time reductions of about 7.1 seconds (utilizing continuous aspiration 732 shown in FIG. 13A), 17.7 seconds (utilizing the continuous aspiration 732 shown in FIG. 13B), 21.3 seconds (utilizing the continuous aspiration 732 shown in FIG. 13C) and 27.3 seconds (utilizing the continuous aspiration 732 shown in FIG. 13D). Faster processing times compared to standard T5 processing times were achieved while also achieving comparable levels of large clusters and cell counts when compared to levels obtained with the standard T5 sipping process as shown in FIGS. 14A-B.

As shown in FIG. 14C, these faster processing times can result in higher vial throughput. In the illustrated example, embodiments were able to process 28.6 vials per hour whereas the standard T5 system utilizing sips was able to process 27.1 vials per hour.

Thus, these tests and data demonstrate the effectiveness of embodiments to collect cells more quickly to achieve desired filter coverage levels while improving or achieving comparable cell clustering that result from use of known slide processing systems. These processing time savings achieved with embodiments can be compounded for each specimen slide to be produced to result in significantly faster preparation and review of specimen slides. For example, embodiments utilizing continuous aspiration and slurps appear capable of substantial time savings compared to standard sipping methods for increased vial and slide throughput.

Although particular embodiments for controlling aspiration rate have been shown and described, it should be understood that the above discussion is not intended to limit the scope of these embodiments. While embodiments and variations of the many aspects of the invention have been disclosed and described herein, such disclosure is provided for purposes of explanation and illustration only. Thus, various changes and modifications may be made without departing from the scope of the claims.

For example, it should be understood that one or multiple and different combinations of continuous vacuum parameters (amplitude, duration and/or duty cycle of pulses that form continuous vacuum) may be controlled according to embodiments. Further, continuous vacuum may be generated in different ways including by direct application of vacuum and use of signal generators and pulse trains having millisecond durations. Further, pulse parameters such as frequency and duty cycle may vary in order to form a desired extended duration, continuous vacuum for extended duration, continuous aspiration. Further, while certain embodiments are described with reference to follow-up vacuum pulses having durations that are shorter than the continuous vacuum, the durations of these pulses may vary depending on, e.g., cellularity.

Moreover, embodiments directed to aspiration rate control may be implemented using only amplitude control, only duration control, or both amplitude and duration control of extended duration, continuous vacuum.

Further, embodiments may involve detecting vacuum decay or changes in air flow in connection with determining filter coverage. Other embodiments may involve determining cellular densities using a laser, ultrasound or other forms of energy that are directed to a specimen such that a comparison of transmitted and reflected energy is indicative of cellular density.

Also, where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially.

What is claimed is:

1. A method for collecting cells on a filter, comprising:
    positioning the filter in a specimen fluid containing suspended cells of a biological specimen;
    determining a maximum rate of aspiration of the specimen fluid across the filter by
        applying one or more initial vacuum pulses across the filter to draw specimen fluid across the filter such that the cells cover at least a portion of the filter,
        determining a filter coverage quantity as a result of the one or more initial vacuum pulses, and
        selecting a maximum rate of aspiration from a pre-determined data set corresponding to the determined filter coverage quantity, wherein the data set comprises a range of maximum rates of aspiration corresponding to pre-selected filter coverage quantities;
    selecting from the data set at least one of a maximum amplitude of vacuum and a maximum duration of vacuum corresponding to the determined maximum rate of aspiration; and
    applying a further vacuum pulse across the filter to collect cells on the filter while controlling an amplitude and a duration of the further vacuum to correspond to the at least one of the selected maximum amplitude of vacuum and the selected maximum duration of vacuum.

2. The method of claim 1, wherein determining the maximum rate of aspiration further comprises
    performing pulsatile aspiration of the specimen fluid across the filter during the application of the one or more initial vacuum pulses; and
    determining the filter coverage quantity during the pulsatile aspiration.

3. The method of claim 2, further comprising
    applying a plurality of initial vacuum pulses to perform intermittent or periodic pulsatile aspiration of specimen fluid across the filter; and
    determining the filter coverage quantity during each pulsatile aspiration of the specimen fluid and choosing one of the respective filter coverage quantities.

4. The method of claim 3, wherein applying a plurality of initial vacuum pulses further comprises applying three initial vacuum pulses to the filter to perform three pulsatile aspirations of the specimen fluid, and wherein the filter coverage quantity is determined during the third pulsatile aspiration.

5. The method of claim 1, wherein the duration of the further vacuum pulse is substantially longer than a duration of any of the one or more initial vacuum pulses.

6. The method of claim 1, wherein the duration of each of the initial vacuum pulses is less than about two seconds, and the duration of the further vacuum pulse is greater than about five seconds.

7. The method of claim 1, wherein the amount of specimen fluid flowing through the filter during application of the further vacuum pulse is substantially greater than the amount of specimen fluid flowing through the filter during application of any of the one or more initial vacuum pulses.

8. The method of claim 1, wherein the amplitude of the further vacuum pulse increases for a time period of about five to ten seconds, and wherein the amplitude of each of the one or more initial vacuum pulses substantially decays within about two seconds.

9. The method of claim 1, wherein an area bounded by a curve representing the amplitude of the further vacuum pulse over time is substantially greater than an area bounded by a curve representing an amplitude of any of the one or more initial vacuum pulses over time.

10. The method of claim 1, further comprising
applying an additional vacuum pulse through the filter after application of the further vacuum pulse, and
collecting additional cells on the filter until a pre-determined filter coverage quantity is reached, the additional vacuum pulse having a duration substantially shorter than the duration of the further vacuum pulse.

11. The method of claim 1, wherein the filter coverage quantity is determined utilizing a rate of decay of the initial vacuum pulse as cells are collected on the filter.

12. The method of claim 1, wherein filter coverage quantity is determined utilizing a flow sensor to detect a change of air flow through the filter as cells are collected on the filter.

13. The method of claim 1, the further vacuum pulse being generated by low duty cycle vacuum pulses having durations that are substantially shorter than a duration of any of the one or more initial vacuum pulses.

14. The method of claim 13, the low duty cycle vacuum pulses each having a duration on an order of milliseconds, and any of the one or more initial vacuum pulses having a duration on an order of seconds.

15. The method of claim 14, the low duty cycle vacuum pulses having a respective duty cycle of about 3% to about 15%.

16. A method for collecting cells on a filter, the method comprising:
positioning the filter in a specimen fluid containing suspended cells of a biological specimen;
applying a series of initial vacuum pulses to cause pulsatile aspiration of the specimen fluid across the filter such that the cells cover at least a portion of the filter;
determining a maximum rate of aspiration of the specimen fluid across the filter based at least in part upon
a filter coverage quantity determined as a result of the applied pulsatile aspiration of the specimen fluid across the filter, and
a maximum rate of aspiration selected from a pre-determined data set that corresponds to the determined filter coverage quantity;
determining an amplitude and a duration of a further vacuum pulse to be applied across the filter based at least in part upon at least one of a maximum amplitude of vacuum and a maximum of duration of vacuum selected from the data set that correspond to the determined maximum rate of aspiration; and
applying the further vacuum pulse across the filter to collect cells on the filter while controlling the amplitude and the duration of the further vacuum pulse to correspond to the at least one of the maximum amplitude of vacuum and the maximum duration of vacuum.

17. The method of claim 16, wherein applying the series of initial vacuum pulses to cause pulsatile aspiration of the specimen fluid across the filter comprises applying a plurality of vacuum pulses to cause intermittent or periodic pulsatile aspiration of specimen fluid across the filter.

18. The method of claim 17, wherein the filter coverage quantity is determined by determining a respective filter coverage quantity during each pulsatile aspiration of the specimen fluid, and selecting one of the respective determined filter coverage quantities.

19. The method of claim 16, wherein the filter coverage quantity is determined utilizing a rate of decay of any one of the pulses in the series of initial vacuum pulses as cells collect on the filter.

20. The method of claim 16, wherein the filter coverage quantity is determined by utilizing a flow sensor to detect a change of air flow through the filter as cells collect on the filter.

* * * * *